US010022207B2

(12) United States Patent
Taylor et al.

(10) Patent No.: US 10,022,207 B2
(45) Date of Patent: Jul. 17, 2018

(54) ORAL IRRIGATOR WITH SLIDE PAUSE SWITCH

(71) Applicant: WATER PIK, INC., Fort Collins, CO (US)

(72) Inventors: Kurt M. Taylor, Fort Collins, CO (US); Harold A. Luettgen, Windsor, CO (US); Jeremy James Johnson, Longmont, CO (US)

(73) Assignee: Water Pik, Inc., Fort Collins, CO (US)

( * ) Notice: Subject to any disclaimer, the term of this patent is extended or adjusted under 35 U.S.C. 154(b) by 790 days.

(21) Appl. No.: 14/555,339

(22) Filed: Nov. 26, 2014

(65) Prior Publication Data
US 2015/0147717 A1 May 28, 2015

Related U.S. Application Data

(60) Provisional application No. 61/909,738, filed on Nov. 27, 2013.

(51) Int. Cl.
*A61C 17/02* (2006.01)
(52) U.S. Cl.
CPC ...... *A61C 17/0202* (2013.01); *A61C 17/0205* (2013.01)
(58) Field of Classification Search
CPC . A61C 17/0202; A61C 17/34; A61C 17/0205; A61C 17/20; A61C 17/224; A61C 1/0092
See application file for complete search history.

(56) References Cited

U.S. PATENT DOCUMENTS

| 555,588 A | 3/1896 | Spencer |
| 1,278,225 A | 9/1918 | Schamberg |
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,602,742 A | 10/1926 | Bennet |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |

(Continued)

FOREIGN PATENT DOCUMENTS

| CA | 851479 | 9/1970 |
| CH | 655237 | 4/1986 |

(Continued)

OTHER PUBLICATIONS

US RE27,274, 01/1972, Mattingly (withdrawn)
(Continued)

*Primary Examiner* — Quang D Thanh
(74) *Attorney, Agent, or Firm* — Dorsey & Whitney LLP

(57) ABSTRACT

An oral irrigator including a handle through which fluid flows to a tip. Fluid flows to the tip during irrigate mode, and fluid flow may be interrupted by selecting a pause mode. The handle includes a mechanically controlled actuator for selecting the pause mode. The actuator may include a rack gear operably connected to a pinion gear formed on a valve spool inside the handle. The valve spool may include a ball that blocks fluid flow to the tip during pause mode but not during irrigate mode.

18 Claims, 24 Drawing Sheets

(56) References Cited

U.S. PATENT DOCUMENTS

| | | |
|---|---|---|
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,733,713 A | 2/1956 | Kabnick |
| 2,783,919 A | 3/1957 | Ansell |
| 2,794,437 A | 6/1957 | Tash |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,202 S | 11/1967 | Fulton et al. |
| D209,203 S | 11/1967 | Mattingly et al. |
| D209,204 S | 11/1967 | St Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A | 9/1969 | Ostrowsky |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A | 3/1973 | Buchtel et al. |
| 3,747,595 A | 7/1973 | Grossan |
| 3,768,472 A | 10/1973 | Hodosh et al. |
| 3,771,186 A | 11/1973 | Moret et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,911,796 A | 10/1975 | Hull et al. |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,022,114 A | 5/1977 | Hansen, III et al. |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A | 1/1979 | Boyd et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,210,380 A | 7/1980 | Brzostek |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |

(56) References Cited

U.S. PATENT DOCUMENTS

| | | |
|---|---|---|
| 4,382,786 A | 5/1983 | Lohn |
| D270,000 S | 8/1983 | Ketler |
| 4,396,011 A | 8/1983 | Mack et al. |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,810,148 A | 3/1989 | Aisa et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,864,918 A | 9/1989 | Martin |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kandler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A * | 1/1994 | Jousson ............. A61C 17/0202 433/80 |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |

(56) References Cited

U.S. PATENT DOCUMENTS

| | | | |
|---|---|---|---|
| 5,317,691 A | 5/1994 | Traeger | |
| 5,321,865 A * | 6/1994 | Kaeser | A61C 17/36 15/22.1 |
| 5,323,770 A | 6/1994 | Ito et al. | |
| 5,331,704 A | 7/1994 | Rosen et al. | |
| 5,344,317 A | 9/1994 | Pacher et al. | |
| 5,346,677 A | 9/1994 | Risk | |
| 5,349,896 A | 9/1994 | Delaney | |
| D351,892 S | 10/1994 | Wolf et al. | |
| 5,360,338 A | 11/1994 | Waggoner | |
| 5,368,548 A | 11/1994 | Jousson | |
| 5,370,534 A | 12/1994 | Wolf et al. | |
| D354,168 S | 1/1995 | Hartwein | |
| D354,559 S | 1/1995 | Knute | |
| 5,378,149 A | 1/1995 | Stropko | |
| 5,380,201 A | 1/1995 | Kawata | |
| D356,864 S | 3/1995 | Woog | |
| 5,399,089 A * | 3/1995 | Eichman | A61C 17/02 433/80 |
| D358,883 S | 5/1995 | Vos | |
| 5,456,672 A | 10/1995 | Diederich et al. | |
| 5,465,445 A | 11/1995 | Yeh | |
| 5,467,495 A | 11/1995 | Boland et al. | |
| 5,468,148 A | 11/1995 | Ricks | |
| 5,470,305 A | 11/1995 | Arnett et al. | |
| 5,474,450 A | 12/1995 | Chronister | |
| 5,474,451 A | 12/1995 | Dalrymple et al. | |
| 5,476,379 A | 12/1995 | Disel | |
| 5,484,281 A * | 1/1996 | Renow | A61C 17/0214 433/80 |
| 5,487,877 A | 1/1996 | Choi | |
| 5,490,779 A | 2/1996 | Malmin | |
| 5,505,916 A | 4/1996 | Berry, Jr. | |
| D369,656 S | 5/1996 | Vos | |
| D370,125 S | 5/1996 | Craft et al. | |
| 5,525,058 A | 6/1996 | Gallant et al. | |
| 5,526,841 A | 6/1996 | Detsch et al. | |
| 5,540,587 A | 7/1996 | Malmin | |
| 5,547,374 A | 8/1996 | Coleman | |
| D373,631 S | 9/1996 | Maeda et al. | |
| 5,554,014 A | 9/1996 | Becker | |
| 5,554,025 A | 9/1996 | Kinsel | |
| 5,556,001 A | 9/1996 | Weissman et al. | |
| 5,564,629 A | 10/1996 | Weissman et al. | |
| D376,893 S | 12/1996 | Gornet | |
| D377,091 S | 12/1996 | Scott, Sr. | |
| 5,613,259 A | 3/1997 | Craft et al. | |
| 5,616,028 A | 4/1997 | Hafele et al. | |
| 5,626,472 A | 5/1997 | Pennetta | |
| 5,634,791 A | 6/1997 | Matsuura et al. | |
| 5,636,987 A | 6/1997 | Serfaty | |
| 5,640,735 A | 6/1997 | Manning | |
| D382,407 S | 8/1997 | Craft et al. | |
| 5,653,591 A | 8/1997 | Loge | |
| 5,659,995 A | 8/1997 | Hoffman | |
| 5,667,483 A | 9/1997 | Santos | |
| D386,576 S | 11/1997 | Wang et al. | |
| 5,683,192 A | 11/1997 | Kilfoil | |
| 5,685,829 A | 11/1997 | Allen | |
| 5,685,851 A | 11/1997 | Murphy et al. | |
| 5,697,784 A | 12/1997 | Hafele et al. | |
| D388,612 S | 1/1998 | Stutzer et al. | |
| D388,613 S | 1/1998 | Stutzer et al. | |
| D389,091 S | 1/1998 | Dickinson | |
| 5,709,545 A | 1/1998 | Johnston et al. | |
| D390,934 S | 2/1998 | McKeone | |
| 5,716,007 A | 2/1998 | Nottingham et al. | |
| 5,718,668 A | 2/1998 | Arnett et al. | |
| 5,746,595 A | 5/1998 | Ford | |
| 5,749,726 A | 5/1998 | Kinsel | |
| 5,759,502 A | 6/1998 | Spencer et al. | |
| 5,779,471 A | 7/1998 | Tseng et al. | |
| 5,779,654 A | 7/1998 | Foley et al. | |
| 5,795,153 A | 8/1998 | Rechmann | |
| 5,796,325 A | 8/1998 | Lundell et al. | |
| 5,833,065 A | 11/1998 | Burgess | |
| 5,836,030 A | 11/1998 | Hazeu et al. | |
| D402,744 S | 12/1998 | Zuege | |
| 5,851,079 A | 12/1998 | Horstman et al. | |
| D403,511 S | 1/1999 | Serbinski | |
| D406,334 S | 3/1999 | Rosenthal et al. | |
| 5,876,201 A | 3/1999 | Wilson et al. | |
| D408,511 S | 4/1999 | Allen et al. | |
| 5,901,397 A | 5/1999 | Häfele et al. | |
| 5,934,902 A | 8/1999 | Abahusayn | |
| D413,975 S | 9/1999 | Maeda | |
| D416,999 S | 11/1999 | Miyamoto | |
| D417,082 S | 11/1999 | Classen et al. | |
| 5,993,402 A | 11/1999 | Sauer et al. | |
| 6,030,215 A | 2/2000 | Ellion et al. | |
| 6,038,960 A | 3/2000 | Fukushima et al. | |
| 6,039,180 A | 3/2000 | Grant | |
| 6,047,429 A | 4/2000 | Wu | |
| D424,181 S | 5/2000 | Caplow | |
| D425,615 S | 5/2000 | Bachman et al. | |
| D425,981 S | 5/2000 | Bachman et al. | |
| 6,056,548 A | 5/2000 | Neuberger et al. | |
| 6,056,710 A | 5/2000 | Bachman et al. | |
| D426,633 S | 6/2000 | Bachman et al. | |
| 6,089,865 A | 7/2000 | Edgar | |
| 6,116,866 A | 9/2000 | Tomita et al. | |
| 6,120,755 A | 9/2000 | Jacobs | |
| 6,124,699 A | 9/2000 | Suzuki et al. | |
| D434,500 S | 11/2000 | Pollock et al. | |
| 6,159,006 A | 12/2000 | Cook et al. | |
| 6,164,967 A | 12/2000 | Sale et al. | |
| D435,905 S | 1/2001 | Bachman et al. | |
| D437,049 S | 1/2001 | Hartwein | |
| 6,193,512 B1 | 2/2001 | Wallace | |
| 6,193,932 B1 | 2/2001 | Wu et al. | |
| 6,199,239 B1 | 3/2001 | Dickerson | |
| 6,200,134 B1 | 3/2001 | Kovac | |
| D439,781 S | 4/2001 | Spore | |
| 6,217,835 B1 | 4/2001 | Riley et al. | |
| D441,861 S | 5/2001 | Hafliger | |
| 6,233,773 B1 | 5/2001 | Karge et al. | |
| 6,234,205 B1 | 5/2001 | D'Amelio et al. | |
| 6,237,178 B1 | 5/2001 | Krammer et al. | |
| 6,247,929 B1 * | 6/2001 | Bachman | A61C 17/0202 433/80 |
| 6,280,190 B1 | 8/2001 | Hoffman | |
| D448,236 S | 9/2001 | Murray | |
| 6,293,792 B1 | 9/2001 | Hanson | |
| D449,884 S | 10/2001 | Tobin et al. | |
| 6,299,419 B1 | 10/2001 | Hunklinger | |
| D453,453 S | 2/2002 | Lun | |
| D455,201 S | 4/2002 | Jones | |
| D455,203 S | 4/2002 | Jones | |
| 6,363,565 B1 | 4/2002 | Paffrath | |
| D457,949 S | 5/2002 | Krug | |
| D464,799 S | 10/2002 | Crossman et al. | |
| 6,468,482 B1 | 10/2002 | Frieze et al. | |
| 6,475,173 B1 | 11/2002 | Bachman et al. | |
| 6,485,451 B1 | 11/2002 | Roberts et al. | |
| 6,497,375 B1 | 12/2002 | Srinath et al. | |
| 6,497,572 B2 | 12/2002 | Hood et al. | |
| 6,502,584 B1 | 1/2003 | Fordham | |
| D470,660 S | 2/2003 | Schaber | |
| 6,532,837 B1 | 3/2003 | Magussen, Jr. | |
| 6,558,344 B2 | 5/2003 | McKinnon et al. | |
| 6,561,808 B2 | 5/2003 | Neuberger et al. | |
| D475,346 S | 6/2003 | McCurrach et al. | |
| D476,743 S | 7/2003 | D'Silva | |
| 6,589,477 B1 | 7/2003 | Frieze et al. | |
| 6,602,071 B1 | 8/2003 | Ellion et al. | |
| 6,632,091 B1 | 10/2003 | Cise et al. | |
| D482,451 S | 11/2003 | Page et al. | |
| 6,640,999 B2 | 11/2003 | Peterson | |
| 6,647,577 B2 | 11/2003 | Tam | |
| 6,659,674 B2 | 12/2003 | Carlucci et al. | |
| 6,663,386 B1 | 12/2003 | Moelsgaard | |
| 6,669,059 B2 | 12/2003 | Mehta | |
| D484,971 S | 1/2004 | Hartwein | |
| 6,681,418 B1 | 1/2004 | Bierend | |

(56) References Cited

U.S. PATENT DOCUMENTS

| | | |
|---|---|---|
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| 6,808,331 B2 | 10/2004 | Hall et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 | 1/2005 | Blaustein et al. |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,414,337 B2 | 8/2008 | Wilkinson et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D764,051 S | 8/2016 | Wang |
| D774,651 S | 12/2016 | Kaib |
| D776,253 S | 1/2017 | Li |
| D782,326 S | 3/2017 | Fath |
| D782,656 S | 3/2017 | Au |
| D786,422 S | 5/2017 | Au |
| 9,642,677 B2 | 5/2017 | Luettgen et al. |
| D788,907 S | 6/2017 | Kim |
| D798,440 S | 9/2017 | Kim |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1 | 3/2003 | Chang |
| 2003/0098249 A1 | 5/2003 | Rollock |
| 2003/0162146 A1 | 8/2003 | Shortt et al. |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0180569 A1 | 10/2004 | Chiou |
| 2004/0209222 A1 | 10/2004 | Snyder |
| 2005/0049620 A1 | 3/2005 | Chang |
| 2005/0064371 A1 | 3/2005 | Soukos et al. |
| 2005/0101894 A1 | 5/2005 | Hippensteel |

(56) References Cited

U.S. PATENT DOCUMENTS

| | | |
|---|---|---|
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0207052 A1 | 9/2006 | Tran |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0189951 A1 | 8/2008 | Molema et al. |
| 2008/0213719 A1 | 9/2008 | Giniger et al. |
| 2008/0253906 A1 | 10/2008 | Strong |
| 2009/0070949 A1 | 3/2009 | Sagel et al. |
| 2009/0071267 A1 | 3/2009 | Mathus et al. |
| 2009/0082706 A1 | 3/2009 | Shaw |
| 2009/0124945 A1 | 5/2009 | Reich et al. |
| 2009/0139351 A1 | 6/2009 | Reichmuth |
| 2009/0163839 A1 | 6/2009 | Alexander |
| 2009/0188780 A1 | 7/2009 | Watanabe |
| 2009/0281454 A1 | 11/2009 | Baker et al. |
| 2010/0010524 A1 | 1/2010 | Barrington |
| 2010/0015566 A1 | 1/2010 | Shaw |
| 2010/0049177 A1 | 2/2010 | Boone, III et al. |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1 | 2/2012 | Snyder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0266396 A1 | 10/2012 | Leung |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0089832 A1 | 4/2013 | Lee |
| 2013/0295520 A1 | 11/2013 | Hsieh |
| 2014/0106296 A1 | 4/2014 | Woodard et al. |
| 2014/0193774 A1 | 7/2014 | Snyder et al. |
| 2014/0259474 A1 | 9/2014 | Sokol et al. |
| 2014/0272769 A1 | 9/2014 | Luettgen et al. |
| 2014/0272782 A1 | 9/2014 | Luettgen et al. |
| 2014/0352088 A1 | 12/2014 | Wu |
| 2015/0004559 A1 | 1/2015 | Luettgen et al. |
| 2015/0147717 A1 | 5/2015 | Taylor et al. |
| 2015/0182319 A1 | 7/2015 | Wagner et al. |
| 2017/0239132 A1 | 8/2017 | Luettgen et al. |

FOREIGN PATENT DOCUMENTS

| | | |
|---|---|---|
| CN | 204049908 | 12/2014 |
| DE | 1466963 | 5/1969 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| DE | 3346651 | 7/1985 |
| EP | 0023672 | 7/1980 |
| EP | 0515983 | 2/1992 |
| EP | 1825827 | 8/2007 |
| FR | 2556954 | 6/1985 |
| FR | 2654627 | 5/1991 |
| GB | 838564 | 6/1960 |
| GB | 1182031 | 2/1970 |
| GB | 2018605 | 10/1979 |
| JP | 2-134150 | 5/1990 |
| JP | 2009-39455 | 2/2009 |
| KR | 20120126265 | 11/2012 |
| WO | WO 95/016404 | 6/1995 |
| WO | WO 01/10327 | 2/2001 |
| WO | WO 04/021958 | 3/2004 |
| WO | WO 04/039205 | 5/2004 |
| WO | WO 2004/060259 | 7/2004 |
| WO | WO 2004/062518 | 7/2004 |
| WO | WO2004/062518 | 7/2004 |
| WO | WO 2008/070730 | 6/2008 |
| WO | WO2008/070730 | 6/2008 |
| WO | WO 2008/157585 | 12/2008 |
| WO | WO 2013/124691 | 8/2013 |

OTHER PUBLICATIONS

Website: http://www.videodirectstore.com/store/merchant.mv?Screen=PROD&Product Code=EW1' . . . , 2 pages, at least as early as Jun. 20, 2003.

iPik Portable Oral Irrigator. AliExpress. Date reviewed: Oct. 5, 2016. <https://www.allexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-yfAeyJa>, 18 pages.

Brite Leafs Professional Portable 2-in-1 Nasal Sinus & Oral Irrigator. Brite Leafs. Copyright date 2012, <http://www.briteleafs.com/product6.html , 1 page.

AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj.

The Right Tool, Electron Fusion Devices, Inc., 2 pages, at least as early as Feb. 1991.

Japanese Packaging, 2 pages, at least as early as Dec. 2002.

Japanese Instruction Brochure, 20 pages, at least as early as Dec. 2002.

Brochure: Woog International, "You have a 98% chance of getting gum disease. Unless you read this.", Lancaster, Pennsylvania, 5 pages, Feb. 1987.

Brochure: Woog International, "We put the control of home dental care back into the hands of the professional", Lancaster, Pennsylvania, 2 pages, Feb. 1987.

Brochure: Woog International, "Products at a Glance: Home Dental Care System" Woog Orajet, 3 pages, at least as early as Dec. 18, 1998.

Website: http://www.just4teeth.com/product/Panasonic/Panasonic_Portable_Irrigator.htm, 2 pages, at least as early as Jun. 20, 2003.

Website: http://www.videodirectstore.com/store/merchant.mv?Screen=PROD&Product Code=EW1' . . . , 2 pages, at least as early as Jun. 20, 2003.

Website: http://products.consumerguide.com/cp/family/review/index.cfm/id/18742, 2 pages, at least as early as Jun. 20, 2003.

Website: http://www.racekarteng.com/images/walbroparts.gif and http://www.muller.net/mullermachine/docs/walbro1.html, 4 pages, at least as early as Jun. 20, 2003.

European Search Report, EPO Application No. 07250799.9, dated Jul. 5, 2007.

(56) References Cited

OTHER PUBLICATIONS

European Search Report, EPO Application No. 07252693.2, 14 pages, dated Apr. 28, 2008.
European Examination Report, EPO Application No. 07250799.9, dated Feb. 5, 2009.
International Search Report, Application No. PCT/US2010/028180, 2 pages, dated May 18, 2010.
International Search Report, PCT/US2010/060800, 2 pages, dated Feb. 11, 2011.
International Search Report, PCT/US2011/052795, 10 pages, dated Jan. 17, 2012.
Waterpik SinuSense Website: http://www.insightsbyapril.com/2012/03/waterpik-natural-remedy-for-sinus.html, 8 pages, retrieved on May 31, 2012.
Waterpik WP 350W Oral Irrigator. Dentist.net. Copyright date 2013. Date accessed: Mar. 30, 2017, 2 pages <http://www.dentalhoo.com/waterpik-wp350.asp>.
iPik Portable Oral Irrigator. AliExpress. Date reviewed: Oct. 5, 2016. <https://www.allexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-ytAeyJa, 18 pages.
Brite Leafs Professional Portable 2-in-1 Nasal Sinus & Oral Irrigator. Brite Leafs. Copyright date 2012, <http://www.briteleafs.com/product6.html>, 1 page.
Ali Express. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.
Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/., 7 pages.
Waterpik ADA Accepted WP-663, posted at amazon.com, earliest date reviewed on Feb. 6, 2014, [online], acquired on Feb 12, 2018. Available from Internet, <URL: https://www.amazon.com/Waterpik-Accepted-WP-663-Aquarius-Flosser/dp/B072JFVXSY/ref=cm_cr_arp_d_product_top?ie=UTF8&th=1> (Year: 2014).
Waterpik Classic Professional Water Flosser, WP-72, posted at amazon.com, earliest date reviewed on Mar 5 2016, [online], acquired on Feb 23, 2018. Available from Internet, <URL: https://www.amazon.com/Waterpik-Classic-Professional-Flosser-WP-72/dp/B00HFQQOU6/ref=cm_cr_arp_d_product_top?ie=UTF8> (Year: 2016).

\* cited by examiner

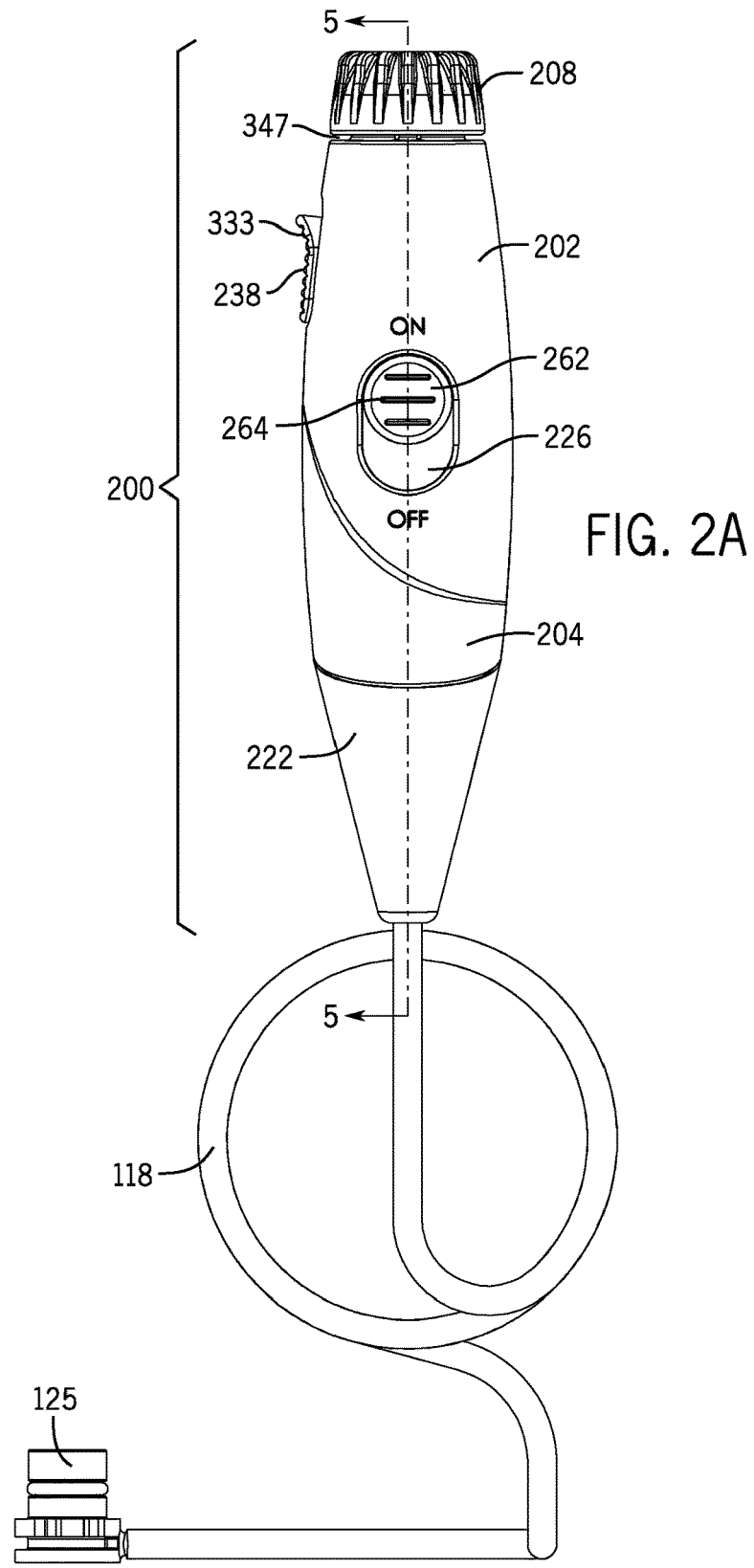

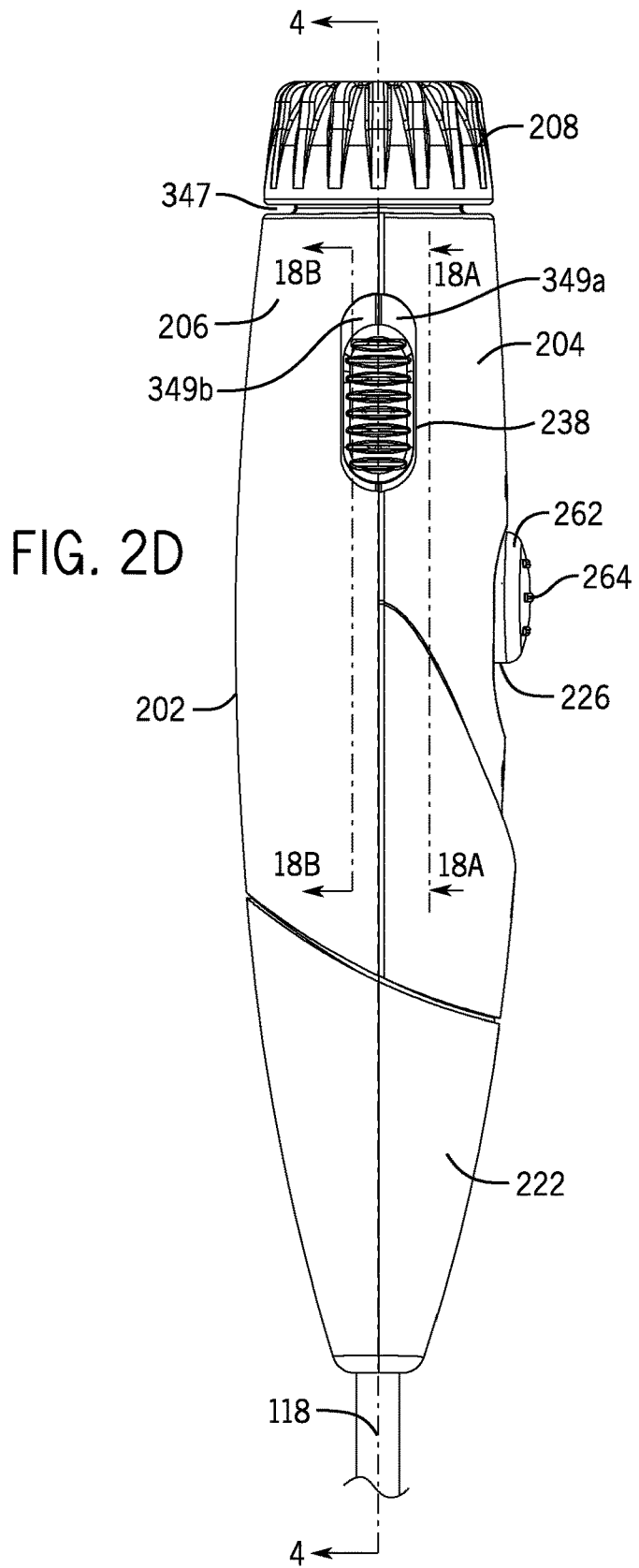

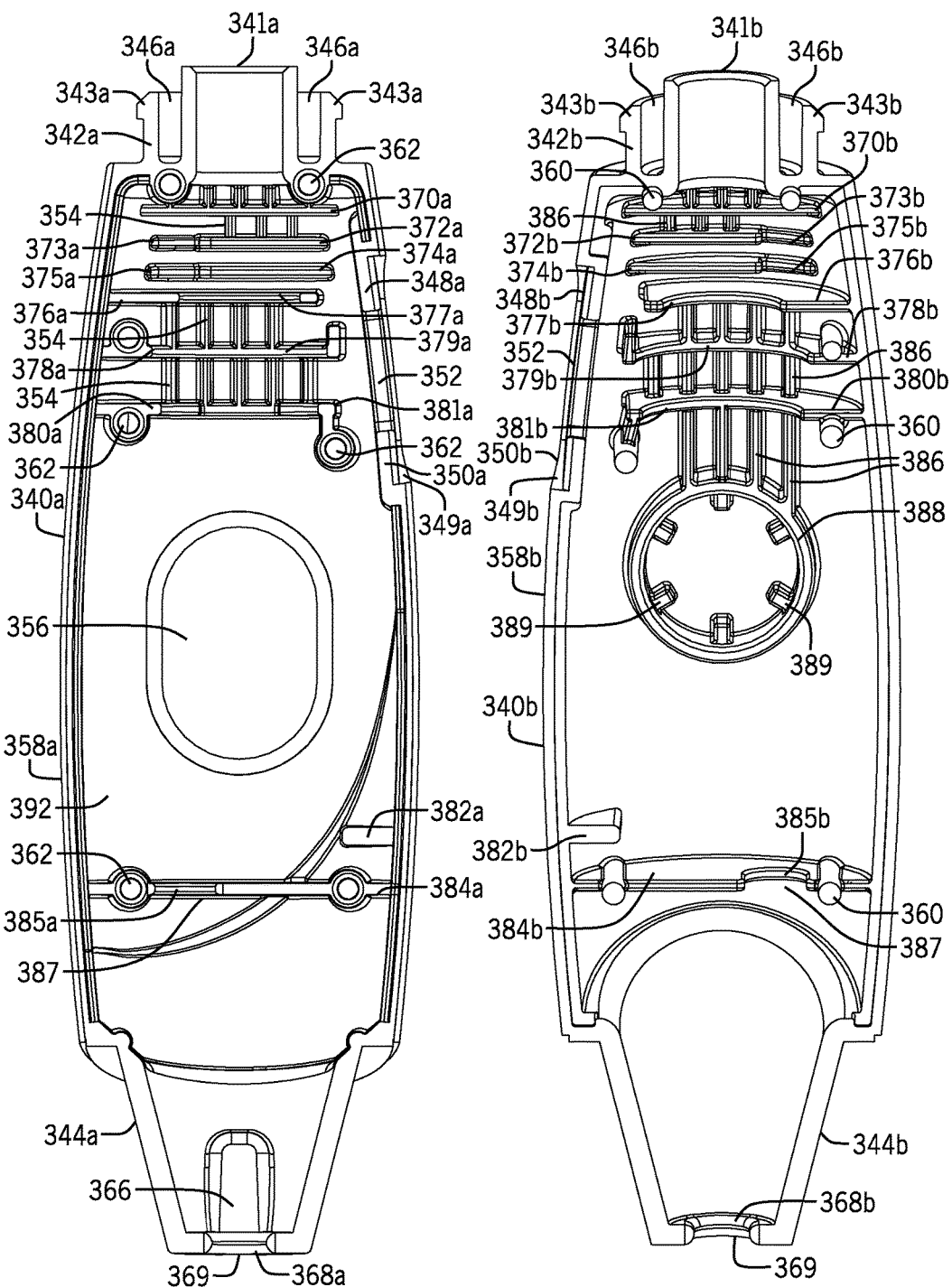

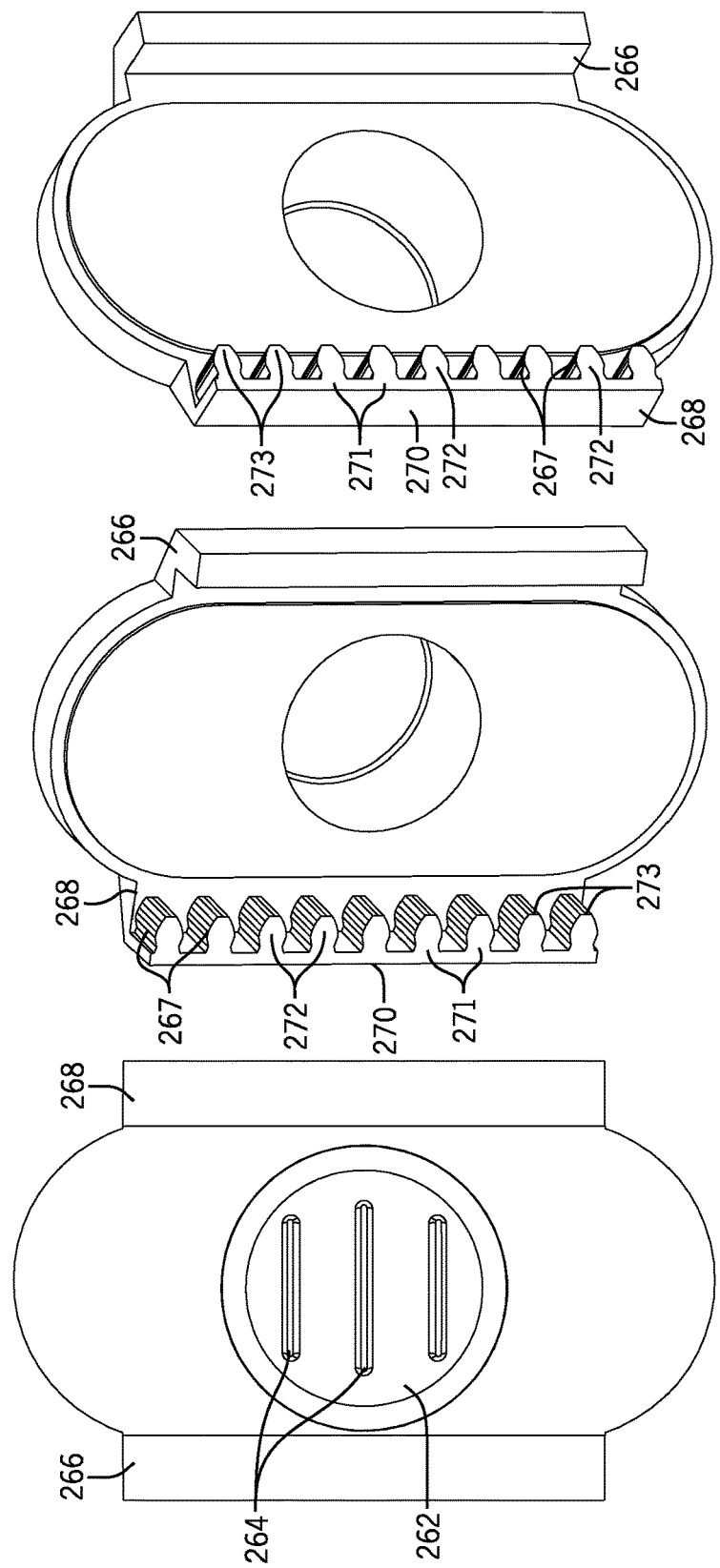

ORAL IRRIGATOR WITH SLIDE PAUSE SWITCH

CROSS-REFERENCE TO RELATED APPLICATIONS

This application claims the benefit of priority pursuant to 35 U.S.C. § 119(e) of U.S. provisional application No. 61/909,738 filed 27 Nov. 2013 entitled "Oral Irrigator with Slide Pause Switch," which is incorporated by reference herein in its entirety.

TECHNICAL FIELD

The present invention relates to health and personal hygiene equipment and more particularly, to oral irrigators.

BACKGROUND

Oral irrigators, or water flossers, typically are used to clean a user's teeth and gums by discharging a pressurized fluid stream into a user's oral cavity. The fluid impacts the teeth and gums to remove debris. Often, the oral irrigator includes a fluid supply, such as a reservoir, that is fluidly connected by a pump to an oral irrigator tip, often through a handle. In some oral irrigators, water flow through the handle can be stopped only by turning off power to the irrigator. Other oral irrigators include actuators to pause fluid flow through the handle without turning off power to the irrigator, but these often include electrical circuitry within the handle and in close proximity to fluid conduits, which creates a safety hazard. Oral irrigators with such electrical actuators are also expensive to manufacture.

SUMMARY

The technology disclosed herein relates to oral irrigators. Oral irrigators may be used to clean a user's teeth and gums by discharging a pressurized fluid stream into a user's oral cavity. The oral irrigator includes a base, a reservoir, and a handle through which fluid flows to an attached tip during irrigate mode. The handle includes a control actuator for selecting a pause mode, which allows a user to interrupt fluid flow to the tip without removing his or her hand from the handle and without turning off power to the oral irrigator. The pause mode is mechanically controlled without electrical components.

In one exemplary embodiment of the oral irrigator disclosed herein, the handle includes a housing, a fluid inlet into the housing, a fluid outlet from the housing, a valve body positioned between the fluid inlet and the fluid outlet, and a valve gear assembly that can be positioned to interrupt fluid flow through the handle. Fluid can flow into the housing through a hose and out of the housing through an attached tip. The valve gear assembly includes a valve gear, which is received in the valve body, and a pause control actuator. In one embodiment, the pause control actuator includes a rack gear that rotates a pinion gear of the valve gear.

In some embodiments, the valve gear includes a ball that can be positioned to block the flow of fluid through the valve body when the pause mode is selected with the pause control actuator. The ball does not block fluid flow through the handle when the irrigate mode is selected with the pause control actuator.

One embodiment of the present disclosure includes an oral irrigator having a reservoir, a pump in fluid communication with the reservoir, a handle in fluid communication with the pump, and a pause switch assembly connected to the handle. The pause switch assembly includes an actuator slidably connected to the handle and movable between a first position and a second position, a valve assembly connected to the actuator and positioned between the handle inlet and the handle outlet. During operation of the pause switch, movement of the actuator from the first position to the second position rotates the valve assembly from an open position to the paused position and in the paused position the valve assembly prevents fluid entering an inlet of the handle from reaching an outlet of the handle.

Another embodiment of the present disclosure includes a handle for an irrigating device. The handle includes a housing in fluid communication with a fluid source and comprising a housing inlet and a housing inlet, a tip removably connected to the housing and n fluid communication with the housing inlet, and a pause switch connected to the housing and configured to selectively interrupt fluid flow from the handle outlet to the handle inlet. The pause switch includes a switch movable along a longitudinal axis of the housing between a first position and a second position and a rotatable sealing assembly connected to the switch. Movement of the switch from the first position to the second position rotates the sealing assembly from an open position to a paused position. In the open position the fluid flows uninterrupted from the handle inlet to the tip and in the paused position the fluid flow is blocked between the handle inlet and the tip.

Yet another embodiment of the present disclosure includes an oral irrigator including a handle, a tip removably connected to the handle housing and a tip release assembly connected to the handle housing. The tip release assembly includes a tip eject button slidably connected to the handle housing and movable between a first position and a second position and a latch connected to the handle housing and positioned within the cavity. Movement of the tip effect button from the first position to the second position moves the latch laterally across the cavity to from an engaged position to a disengaged position. In one example of this embodiment, the movement of the latch is substantially normal to the movement of the tip eject button.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 2A is a front elevation view of a handle of the oral irrigator of FIG. 1A connected to a hose and in irrigate mode.

FIG. 2D is a left elevation view of the handle of FIG. 2A.

FIG. 6 is a rear elevation view of a first housing segment of the handle of FIG. 2A.

FIG. 7 is a front isometric view of a second housing segment of the handle of FIG. 2A.

FIG. 12A is a front elevation view of a pause control actuator of the handle of FIG. 2A.

FIG. 12B is a rear left isometric view of the pause control actuator of FIG. 12A.

FIG. 12C is a rear right isometric view of the pause control actuator of FIG. 12A.

DETAILED DESCRIPTION

An oral irrigator comprising a handle through which fluid flow can be interrupted is disclosed herein. Fluid flow is interrupted by a mechanically controlled pause mode that is safe and convenient for the user. In one exemplary embodiment, manually operating a control actuator slides an attached rack gear, which rotates the coupled pinion gear of a valve gear, which in turn moves a ball inside the valve gear into a position that blocks fluid flow through the handle.

Components of the Oral Irrigator

Figure 1A:
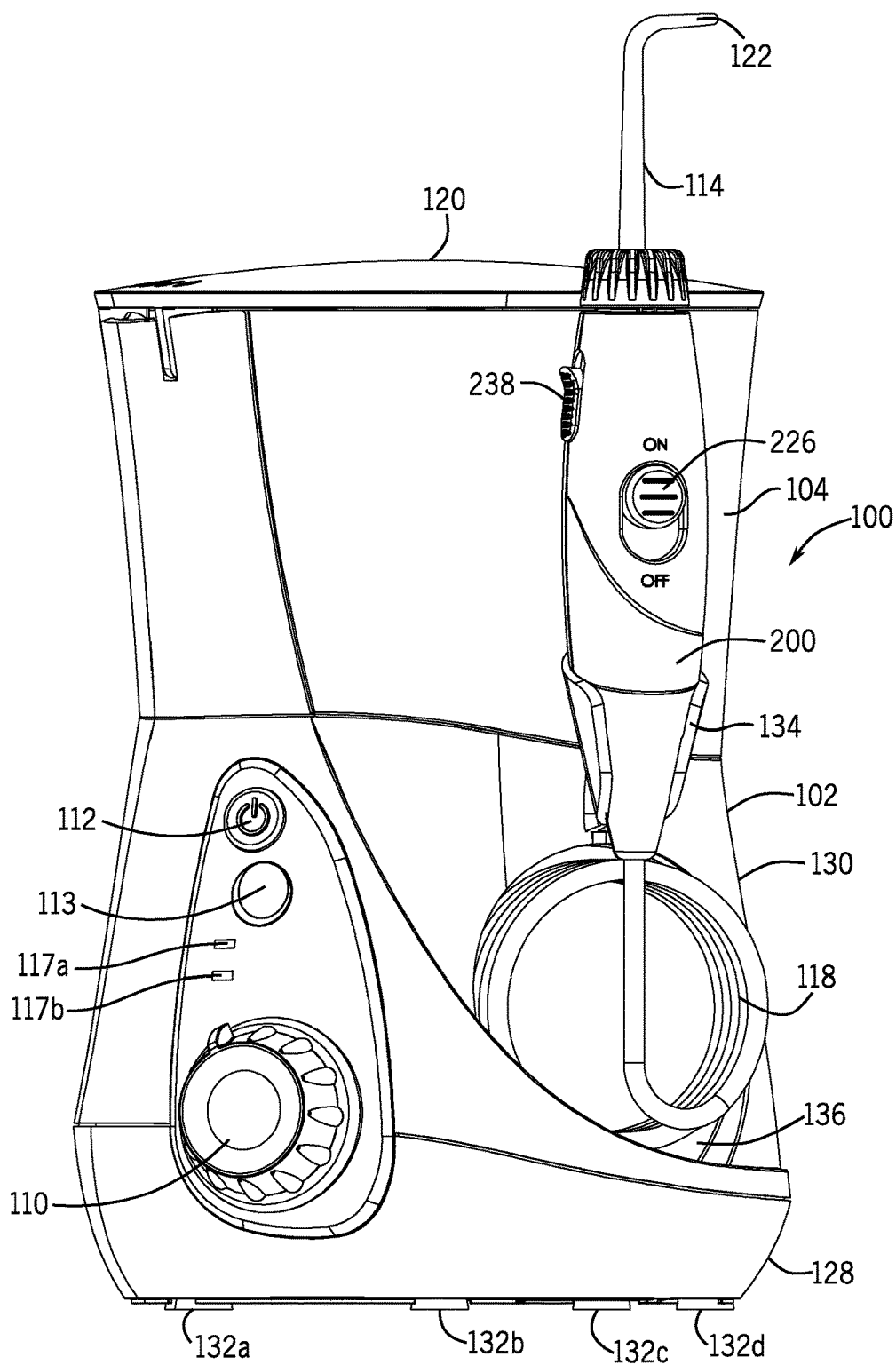
FIG. 1A is a front elevation view of an oral irrigator.
Figure 1B:
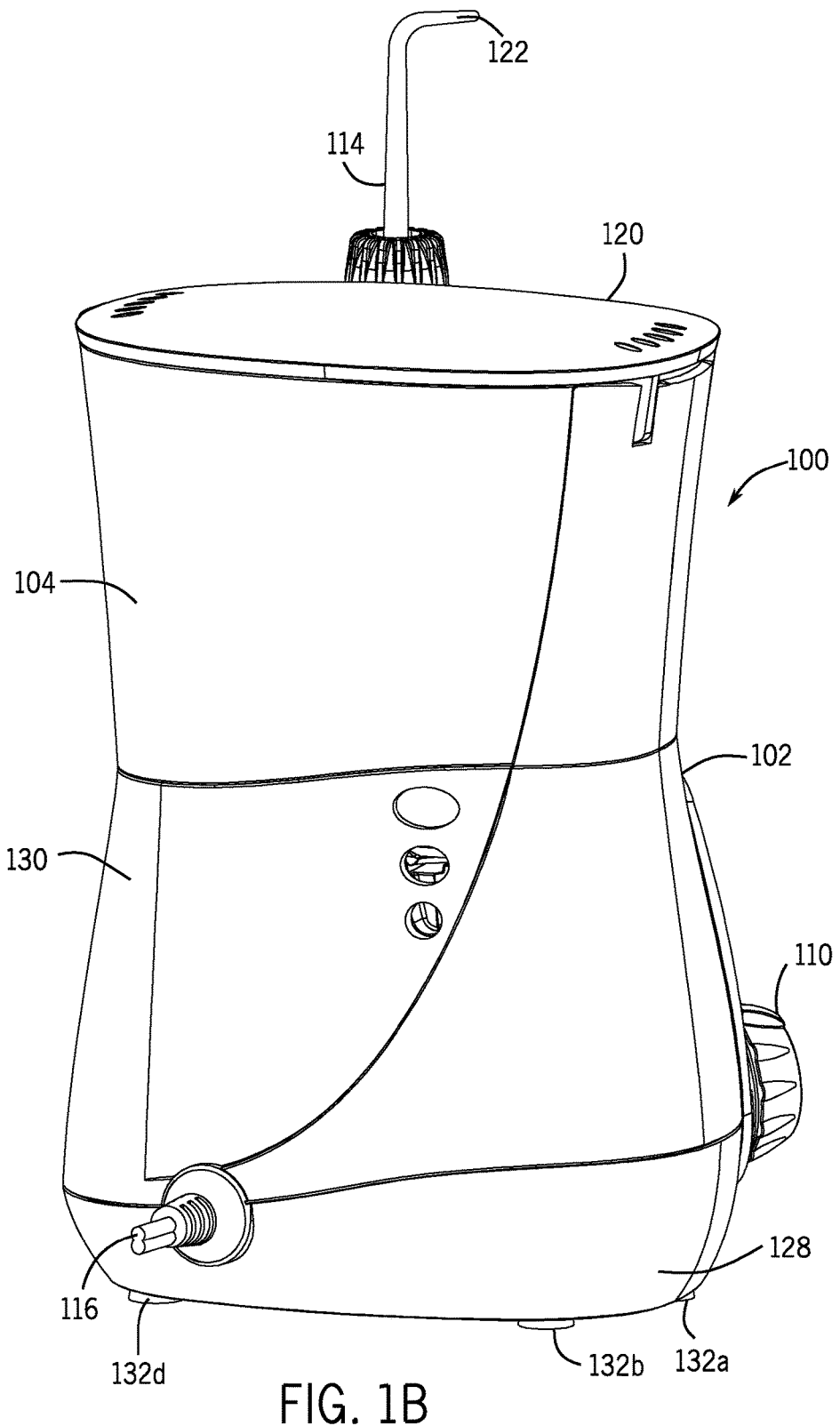
FIG. 1B is a rear isometric view of the oral irrigator of FIG. 1A.
Figure 2B:
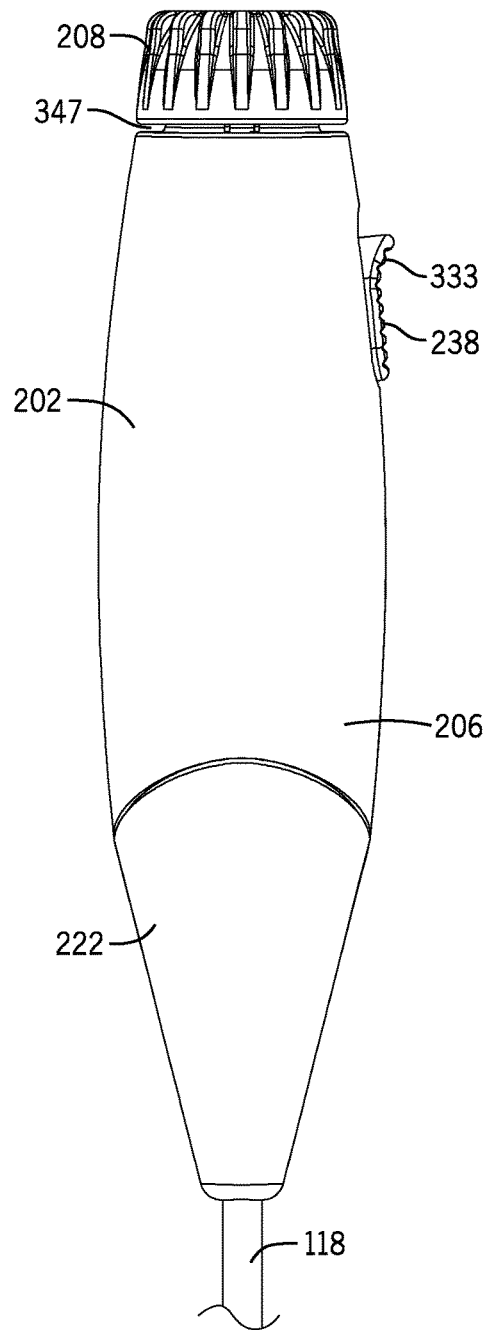
FIG. 2B is a rear elevation view of the handle of FIG. 2A.
Figure 2C:
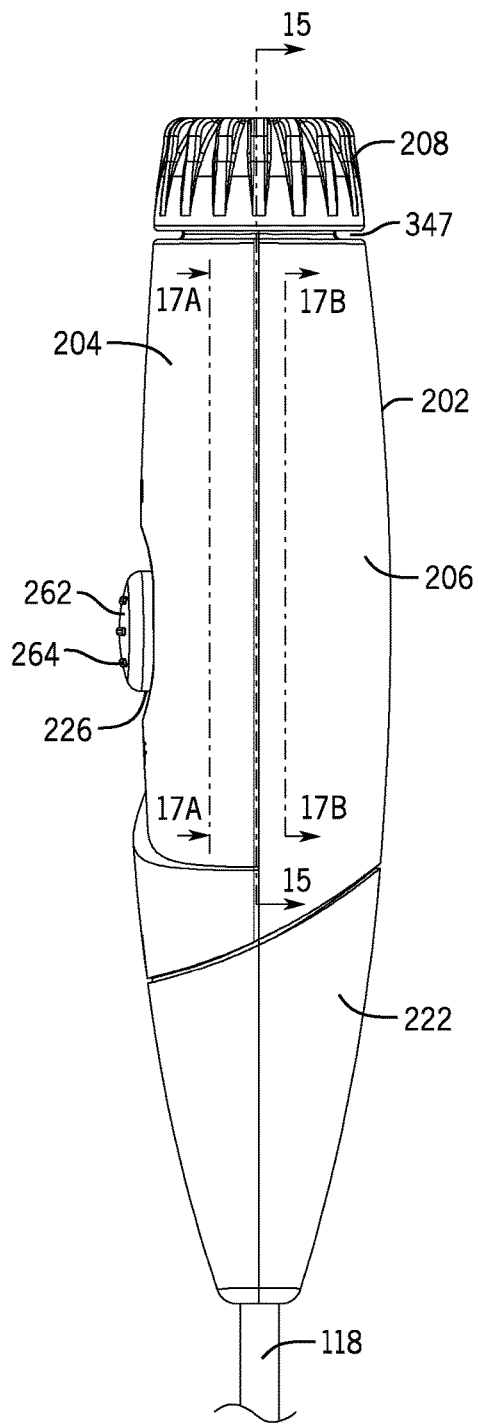
FIG. 2C is a right elevation view of the handle of FIG. 2A, in pause mode.

With reference to FIGS. 1A and 1B, the oral irrigator 100 of the present disclosure may include a base 102, a reservoir 104, and a handle 200. The oral irrigator 100 may also include a lid 120 for the reservoir 104. The base 102 may provide support for the reservoir 104 and the handle 200, as well as house many of the drive and power assembly components of the oral irrigator 100. For example, the base 102 may house a pump, control circuitry, and/or motor.

The base 102 may include a lower base body 128 and an upper base body 130. The lower base body 128 forms a platform or tray that sits within the upper base body 130. The lower base body 128 provides support for one or more of the internal components of the oral irrigator 100 and the upper base body 130 encloses those components to conceal them, as well as provide protection for those components. The base 102 may include a plurality of feet 132a, 132b, 132c, and 132d to support the base 102 on a surface, such as a countertop or the like.

The base 102 may also include a clip 134 or other structure to releasably support the handle 200. In some examples, the clamp 134 may be a C-clip; however, other attachment mechanisms are envisioned. The base 102 may also include a hose cavity 136 or hose box that may receive and support the hose 118 in a coiled position. Although not shown, in some examples, the hose cavity 136 may include one or more arms on which the hose 118 may be wrapped. The hose cavity 136 may be recessed into the upper base body 130, may be flush with the upper base body 130, or may extend outwards from the upper base body 130.

The base 102 may also include a power cable 116 to connect a power source (not shown) to the pump. A first control actuator 112 may be configured to selectively power the oral irrigator 100. For example, the first control actuator 112 may be a power button or knob to turn the oral irrigator 100 on and off.

A second control actuator 110 may be configured to vary a fluid pressure of fluid as it exits a tip 114 on the handle. For example, the second control actuator 110 may be operably connected to a valve assembly within a pump that selectively changes the diameter and/or length of the fluid pathway between reservoir 104 and the tip 114. As the pathway changes, such as due to a user turning the second control actuator 110, the outlet fluid pressure as fluid is expelled from the tip 114 may be selectively modified.

A third control actuator 113 may be configured to selectively activate one or more settings, such as a massage mode, low pressure, or high pressure. In some examples the third control actuator 113 is positioned adjacent to the first control actuator 112 and is a compressible button, rather than a knob. However, in other examples, the third control actuator 113 may be a knob, a switch, or other input element.

With further reference to FIGS. 1A and 1B, the handle 200 is removable from the clip 134 on the base 102 and is in fluid communication with the reservoir 104. For example, the hose 118 fluidly connects the reservoir 104 to the handle 200 via a hose connector 125 such that liquid held in the reservoir 104 can be expelled through the tip 114 connected to the handle 200. As described in more detail below, the handle 200 may be used to vary one or more characteristics of the fluid flow output by the tip 114 separate from or in addition to the features (e.g., the first, second, and third control actuators 112, 110, 113) for controlling the fluid output within the base 102.

The oral irrigator 100 may also include a plurality of indicators 117a, 117b that provide feedback to a user. For example, the indicators 117a, 117b may be one or more light emitting diodes (LEDs) that illuminate, change color, and/or pulse to indicate power to the oral irrigator 100, the current mode, pressure level, or the like.

The tip 114 is selectively removable from the handle 200. For example, and as described in more detail below, a tip eject button 238 can selectively release the tip 114 from the handle 200. The tip 114 defines a fluid pathway 124 that is fluidly connected to the hose 118. The tip 114 includes a tip outlet 122 from which fluid from the reservoir 104 is expelled into a user's mouth from the oral irrigator 100. The tip 114 generally is configured to be inserted into a user's mouth and to expel fluid against a user's teeth, gums, tongue, etc. In some examples, the tip outlet 122 portion of the tip 114 may be shaped as a nozzle or may include a nozzle or other attachment connected thereto. Although a tip 114 is shown, in other embodiments, the oral irrigator 100 may include other accessories, such as a brush head, a nozzle with one or more bristles or cleaning elements, or the like. Accordingly, the discussion of the tip 114 as an outlet for the oral irrigator 100 is meant as illustrative only.

FIGS. 2A-7 depict various views of the handle 200 of the oral irrigator 100. The handle 200 may be defined by a handle housing 202 comprised of a first handle housing segment 204 and a second handle housing segment 206 that are joined together to house additional components of the handle 200. Each of the first and second handle housing segments 204, 206 may be comprised of a neck 342a, 342b, body 340a, 340b, and conical portion 344a, 344b. Some or all of the neck 342a, 342b, body 340a, 340b, and conical portion 344a, 344b may be constructed of a rigid material that resists deformation, such as a hard plastic.

As described in more detail below, the handle 200 may include a generally circular collar 208, the exterior surface of which may be grooved or ribbed. The interior surface of the collar 208 may define a first tip-receiving aperture 209 for receiving the tip 114. A first spring 210 may be positioned in or under the collar 208, such as by being inserted into an annular well defined in the collar 208 or molded into the collar 208 (see FIGS. 4 and 5).

The neck 342a, 342b of each handle housing segment 204, 206 comprises a tip receiving portion 341a, 341b configured to receive a tip 114. The neck 342a, 342b also includes an annular recess 346a, 346b for receiving the first spring 210. When the handle 200 is assembled, the collar 208 may be positioned over the neck 342a, 342b and may be secured to the handle housing 202 by several arcuate tabs 345 extending radially inward from a sidewall of the collar 208 that capture an annular lip 343a, 343b of the neck 342a, 342b (see FIGS. 4 and 5A). The arcuate tabs 345 of the collar 208 may be separated from the bodies 340a, 340b of the handle housing segments 204, 206 by a gap 347, the span of which may be decreased by depressing the collar 208 towards the bodies 340a, 340b.

Figure 3:
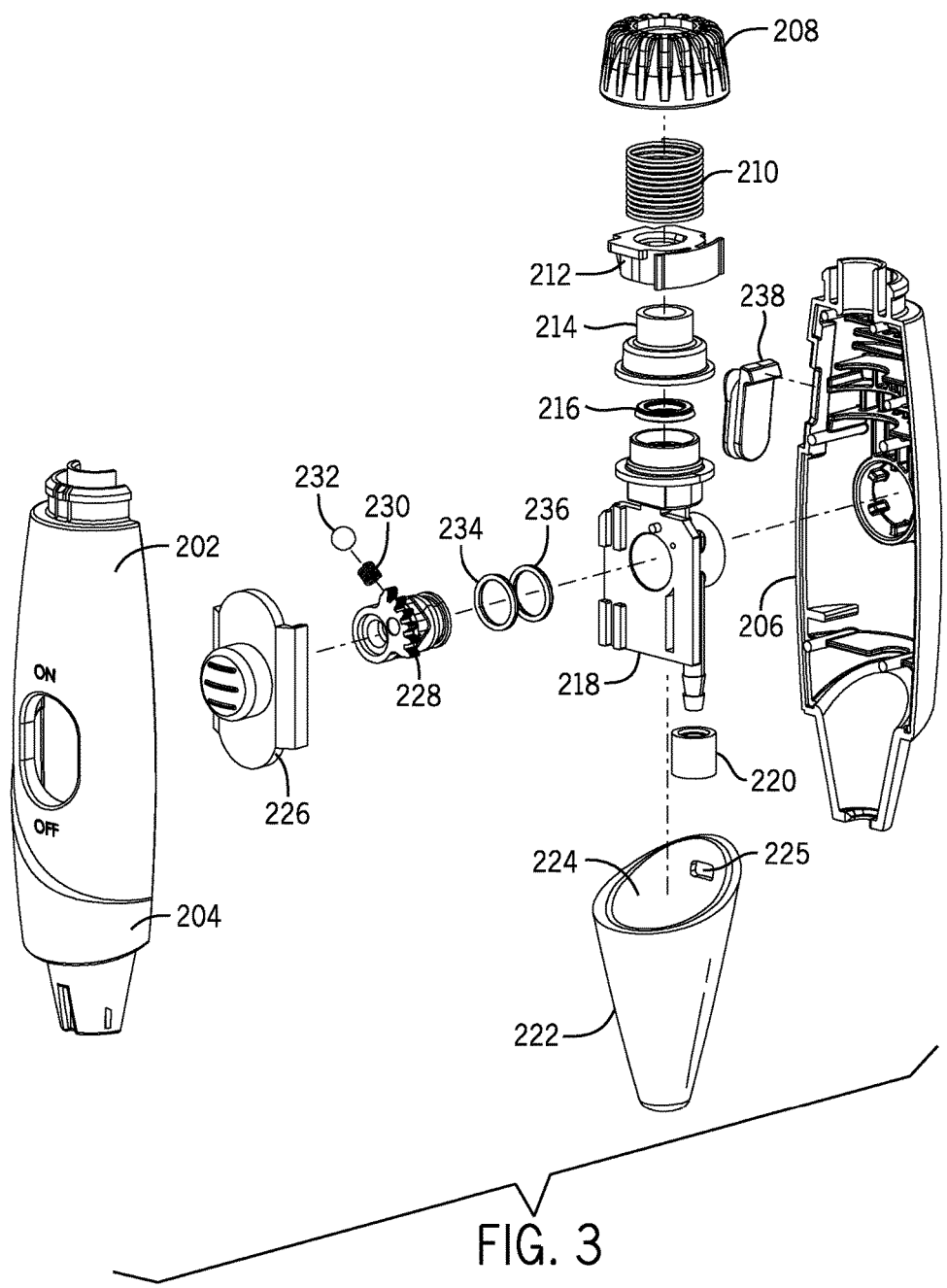
FIG. 3 is an exploded isometric view of the handle of FIG. 2A.

With reference to FIGS. 3, 6, and 7, the bodies 340a, 340b of the first and second handle housing segments 204, 206 together define a handle cavity 392 in which a latch 212, valve cap 214, valve body 218, and hose 118 may reside. The first handle housing segment 204 may include first, second, third, fourth, fifth, sixth, seventh, and eighth shelves 370a, 372a, 374a, 376a, 378a, 380a, 382a, and 384a, respectively, for aligning, receiving, retaining, and/or supporting the latch 212, valve cap 214, valve body 218, and hose 118 within the handle cavity 392 (see FIGS. 4 and 5A). The shelves 370a, 372a, 374a, 376a, 378a, 380a, 382a, and 384a generally extend in a horizontal plane with respect to a longitudinal axis of the handle 200, and radially inwardly from the first handle housing segment 204 within the handle cavity 392. Each shelf 370a, 372a, 374a, 376a, 378a, 380a, 382a, and 384a may align with a mating shelf 370b, 372b, 374b, 376b, 378b, 380b, 382b, and 384b, respectively, extending from the second handle housing segment 206 when the handle 200 is assembled. As in the first handle housing segment 204, the shelves 370b, 372b, 374b, 376b, 378b, 380b, 382b, and 384b of the second handle housing segment 206 help align, receive, retain, and/or support the latch 212, valve cap 214, valve body 218, and hose 118 within the handle cavity 392 (see FIGS. 4 and 5A). Also as in the first handle housing segment 204, the shelves 370b, 372b, 374b, 376b, 378b, 380b, 382b, and 384b of the second handle housing segment 206 generally extend in a horizontal plane with respect to the longitudinal axis of the handle 200, and radially inwardly from the second handle housing segment 206 within the handle cavity 392.

The depth of the shelves 370a,b, 372a,b, 374a,b, 376a,b, 378a,b, 380a,b, 382a,b, and 384a,b may be the same or different, and the depth of a given shelf may vary along the width (the lateral dimension) of that shelf. Each shelf 370a,b, 372a,b, 374a,b, 376a,b, 378a,b, 380a,b, 382a,b, and 384a,b may have an edge facing the handle cavity 392. The edge may be interrupted by a recessed portion 373a,b, 375a,b, 377a,b, 379a,b, 381a,b, and 385a,b. Some of the recessed portions 377a,b, 379a,b, 381a,b, and 385a,b may be formed as a semicircular notch. Opposing semicircular notches 377a,b, 379a,b, 381a,b, and 385a,b align to form generally circular apertures for receiving a portion of the latch 212, valve cap 214, valve body 218, or hose 118.

The bodies 340a, 340b of the first and second handle housing segments 204, 206 may also include vertical support walls 354, 386 for supporting the shelves 370a,b, 372a,b, 374a,b, 376a,b, 378a,b, 380a,b, 382a,b, and 384a,b. The vertical support walls 354, 386 may also help to align, receive, retain, and/or support the latch 212, valve cap 214, valve body 218, and hose 118 within the handle cavity 392. The vertical support walls 354, 386 may be as deep as the shelves 370a,b, 372a,b, 374a,b, 376a,b, 378a,b, 380a,b, 382a,b, and 384a,b they abut, or may be less deep.

The bodies 340a, 340b of the first and second handle housing segments 204, 206 may also include other interior walls for aligning, receiving, retaining, and/or supporting components within the handle cavity 392. For example, the second handle housing segment 206 may include a circular wall 388 with adjacent counterforts 389 extending radially inward from the circular wall 388 for aligning, receiving, retaining, and/or supporting a valve chamber 282 of the valve body 218.

With further reference to FIGS. 3, 6, and 7, one or more pegs 360 may extend from the interior surface of one of the handle housing segments 204, 206 (e.g., in the depicted embodiment, the second handle housing segment 206) proximate the first, fifth, sixth, and eighth interior shelves 370b, 378b, 380b, and 384b. Each peg 360 may extend into the handle cavity 392 beyond a plane defined by a circumferential edge of the exterior wall 358b of the second handle housing segment 206. Each peg 360 may be adapted to mate with a corresponding boss defining holes 362 in the first, fifth, sixth, and eighth interior shelves 370a, 378a, 380a, and 384a, respectively, of the opposing handle housing segment 204, 206 (e.g., in the depicted embodiment, the first handle housing segment 204). The pegs 360 and the holes 362 may be dimensioned such that each peg 360 will relatively snugly fit within its corresponding hole 362. The friction resulting from this fit may resist decoupling of the handle housing segments 204, 206. Alternatively and/or additionally, the first and second handle housing segments 204, 206 may be joined using glue, epoxy, fasteners, sonic welding, any other known method for joining two items, or by a combination of known methods. For example, the pegs 360 may be glued or adhered within the holes 362.

As depicted in FIGS. 2D, 4, 6, and 7, the outer surface of the exterior walls 358a, 358b of the first and second handle housing segments 204, 206 may each define a C-shaped depression 349a, 349b with respective upper surfaces 348a, 348b and lower surfaces 350a, 350b. When the handle housing 202 is assembled, opposing depressions 349a, 349b define a pocket 349 surrounding an opening 352. An elongate tip eject button 238 is formed with an exterior slider portion 332 and an interior slider portion 336 that are separated from each other by a neck 334. The lateral and longitudinal dimensions of the neck 334 are smaller than the related dimensions of the exterior and interior slider portions 332, 336 such that a circumferential channel is formed between the exterior and interior slider portions 332, 336 about the neck 334.

The exterior slider portion 332 of the tip eject button 238 is positioned within the pocket 349, the neck 334 is received within the opening 352, and the interior slider portion 336 is positioned against an interior wall of the housing 202 opposite the pocket 349. The upper surface 348 and lower surface 350 of the pocket 349 extend beyond the length of the tip eject button 238 such that the pocket 349 is longer than the exterior and interior slider portions 332, 336 and the neck 334 is shorter than a longitudinal dimension of the opening 352 in the pocket 349. In this configuration, the tip eject button 238 is both retained within the opening 352 in the pocket 349 and can slide longitudinally within the pocket 349 as the exterior and interior slider portions 332, 336 travel on either side of the upper and lower surfaces 348, 350 of the pocket 349.

With reference again to FIG. 6, the first handle housing segment 204 may also include a control actuator aperture 356 for receiving a pause control actuator 226. In the depicted embodiment, the control actuator aperture 356 is oval-shaped, but may be any shape. By placing the pause control actuator 226 on the handle 200, the user may more easily change settings or pause the oral irrigator 100 while using the oral irrigator 100.

With reference to FIGS. 3, 6, and 7, the conical portion 344a, 344b of each handle housing segment 204, 206 comprises a semicircular notch 368a, 368b and the notches 368a, 368b together define a substantially circular second hose aperture 369 through which the hose 118 passes. The conical portions 344a, 344b may also be configured to secure a liner 224 of a strain relief 222.

The strain relief 222 for the hose 118 may be constructed of a flexible or deformable material, such as an elastomer. The strain relief 222 is designed to isolate stress on the hose 118 at the region where the hose 118 enters the handle housing 202 at the second hose aperture 369 to prevent transfer of any strain on the hose 118 to where the hose 118 connects to the valve body 218. The strain relief 222 may fit snugly around the hose 118 at a first hose aperture 221 in the strain relief 222 through which the hose 118 passes.

The strain relief 222 may be formed about a liner 224 that aids in connection of the strain relief 222 to the handle housing 202. The generally conical liner 224 may be constructed of a relatively rigid material such as a plastic, similar to or the same as the material forming the handle housing 202. The liner 224 may further be formed with features as further described below for engagement with the handle housing 202. The liner 224 may be shorter than the length of the strain relief 222 to allow for flexibility in the area of engagement between the strain relief 222 and the hose 118. The strain relief 222 may be overmolded on the liner 224 or otherwise secured thereto, such as by gluing, fastening, or any other known method for joining two items. The strain relief 222 may fit snugly around the liner 224.

In the embodiment of FIG. 6, the interior surface of the first handle housing segment 204 includes a recess 366 that receives a rib 223 of the liner 224. Also, the exterior surface of the second handle housing segment 206 includes a tab 364 that captures a notch 225 of the liner 224. The liner 224 may fit snugly around the conical portions 334a, 334b of the first and second handle housing segments 204, 206 and thereby connect the strain relief 222 to the handle housing 202.

With reference to FIGS. 3-5A and 8A-8C, after passing through the first and second hose apertures 221, 369, the hose 118 may pass through a third hose aperture 387 formed by mating of the semicircular notches 385a, 385b in the eighth interior shelves 384a, 384b of the first and second handle housing segments 204, 206.

A valve assembly may include a valve body, a valve spool received within the valve body and a sealing assembly connected to and rotatable with the valve spool. The various components of the valve assembly will now be discussed in more detail. A valve body 218 may be positioned within the handle housing 202 above a terminal end of the hose 118. The valve body 218 may be considered to have a lower portion 276 and an upper portion 274 connected to each other by a neck 277. A fluid conduit 286 may extend downward from the lower portion 276 of the valve body 218 in a direction generally aligned with the longitudinal axis of the handle 200.

The end of the hose 118 fits over a barbed tip 288 of the fluid conduit 286 that extends from the valve body 218. A hollow cylindrical hose clamp 220 may clamp the end of the hose 118 against the fluid conduit 286. The hose clamp 220 may be positioned proximate to, and may be supported by, the eighth interior shelves 384a, 384b. A first fluid inlet 289 in the terminus of the barbed tip 288 provides fluid communication between the hose 118 and the valve body 218.

The lower portion 276 of the valve body 218 also comprises a valve chamber 282 on one face, and a valve chamber aperture 283, walls 300, and a post 296 on an opposing face. The walls 300 define a slot 302. The exemplary embodiment of FIGS. 8B and 8C has four walls 300 that are generally rectangular cuboids in shape and are each shorter than the length of the lower portion 276 of the valve body 218, but any number, shape, and length of walls 300 may be included. The post 296 is generally cylindrical in shape and extends normally from the opposing face, but may be any size and shape. In some embodiments, the lower portion 276 also includes a generally circular aperture 298 and an elongate well 304. The lower portion 276 of the valve body 218 is connected to the upper portion 274 at a neck 277.

Figure 8B:
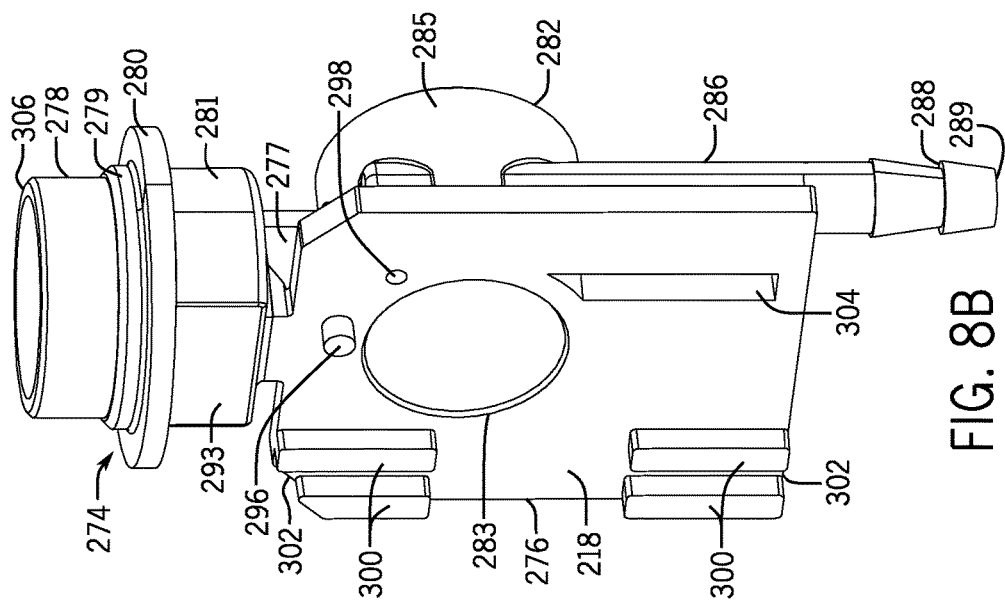
FIG. 8B is a front right isometric view of the valve body of FIG. 8A.
Figure 8A:
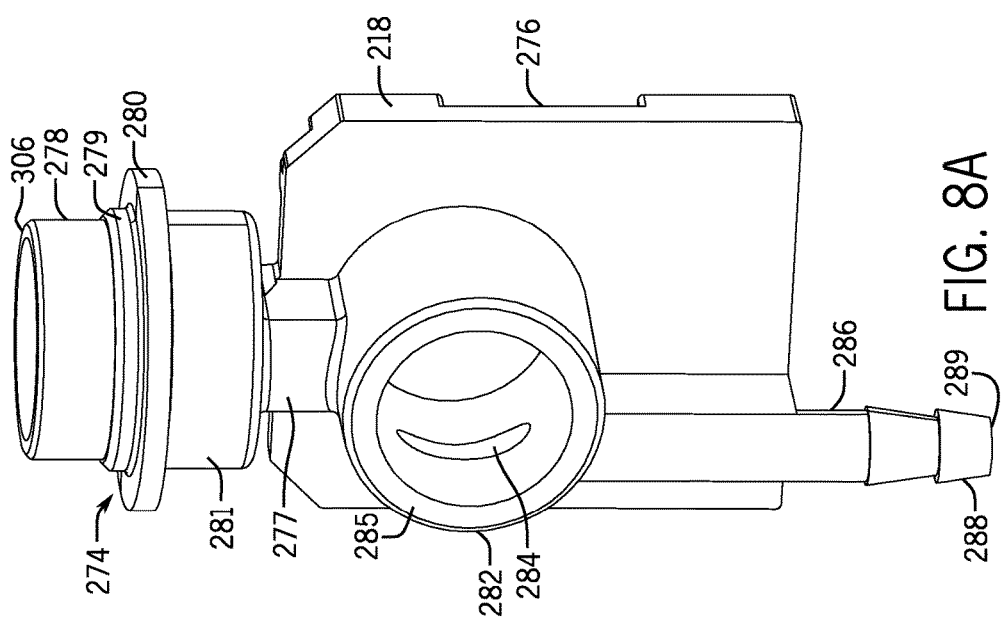
FIG. 8A is a rear left isometric view of a valve body of the handle of FIG. 2A.

The valve chamber 282 is generally cylindrical and extends away from the valve body 218 toward the second handle housing segment 206 in a direction generally aligned with a horizontal axis of the handle 200. The valve chamber 282 is configured to receive a valve spool 228. A second fluid inlet 284 is formed within the chamber wall 285, opens into the valve chamber 282, and is positioned to be in fluid communication with the fluid conduit 286. In the embodiment of FIG. 8A, the second fluid inlet 284 is generally oblong, but may be any size and shape.

A fluid outlet 294 is formed within the chamber wall 285 at a location separated from the second fluid inlet 284, for example, in the direction of the neck 277. The fluid outlet 294 is positioned to be in fluid communication with a well 290 formed in the neck 277 of the valve body 218.

Figure 8C:
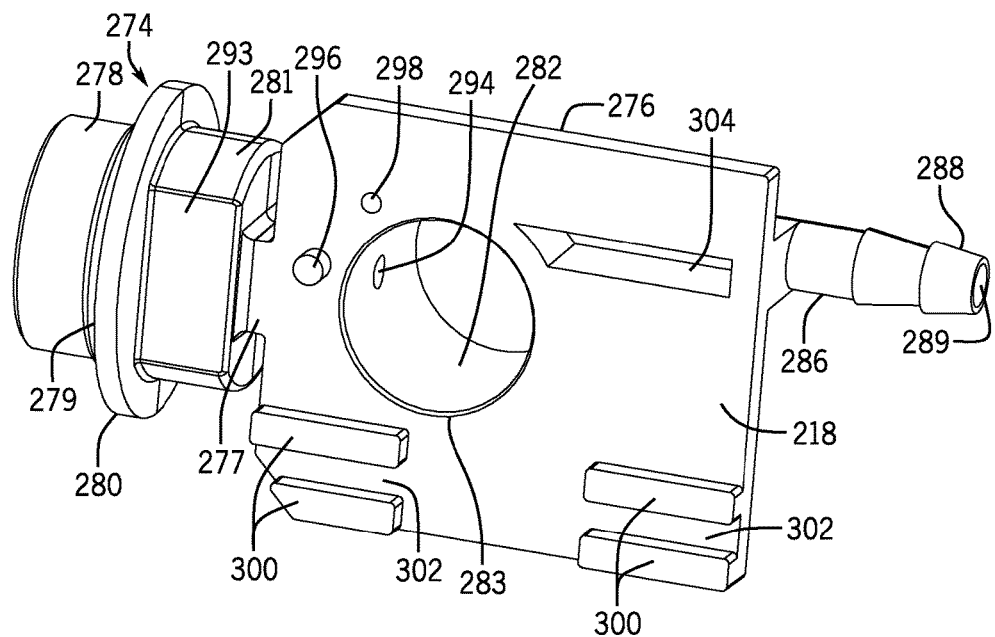
FIG. 8C is a front bottom isometric view of the valve body of FIG. 8A.

The valve spool 228 is received in the valve chamber 282 through a valve chamber aperture 283 on the opposing face of the valve body 218 from which the valve chamber 282 extends. In the embodiment of FIGS. 8B and 8C, the valve chamber aperture 283 is generally circular in shape, but may be any shape that accommodates the valve spool 228.

As depicted in FIGS. 8A-8D, the upper portion 274 of the valve body 218 comprises a mouth 278, a first rim 279, a second rim 280, and a tip receiving portion 281. Each of the mouth 278, first rim 279, and second rim 280 may be generally circular in shape. The second rim 280 may have a greater circumference than the first rim 279, such that the upper portion 274 of the valve body 218 has a stepped outer surface.

Figure 4:
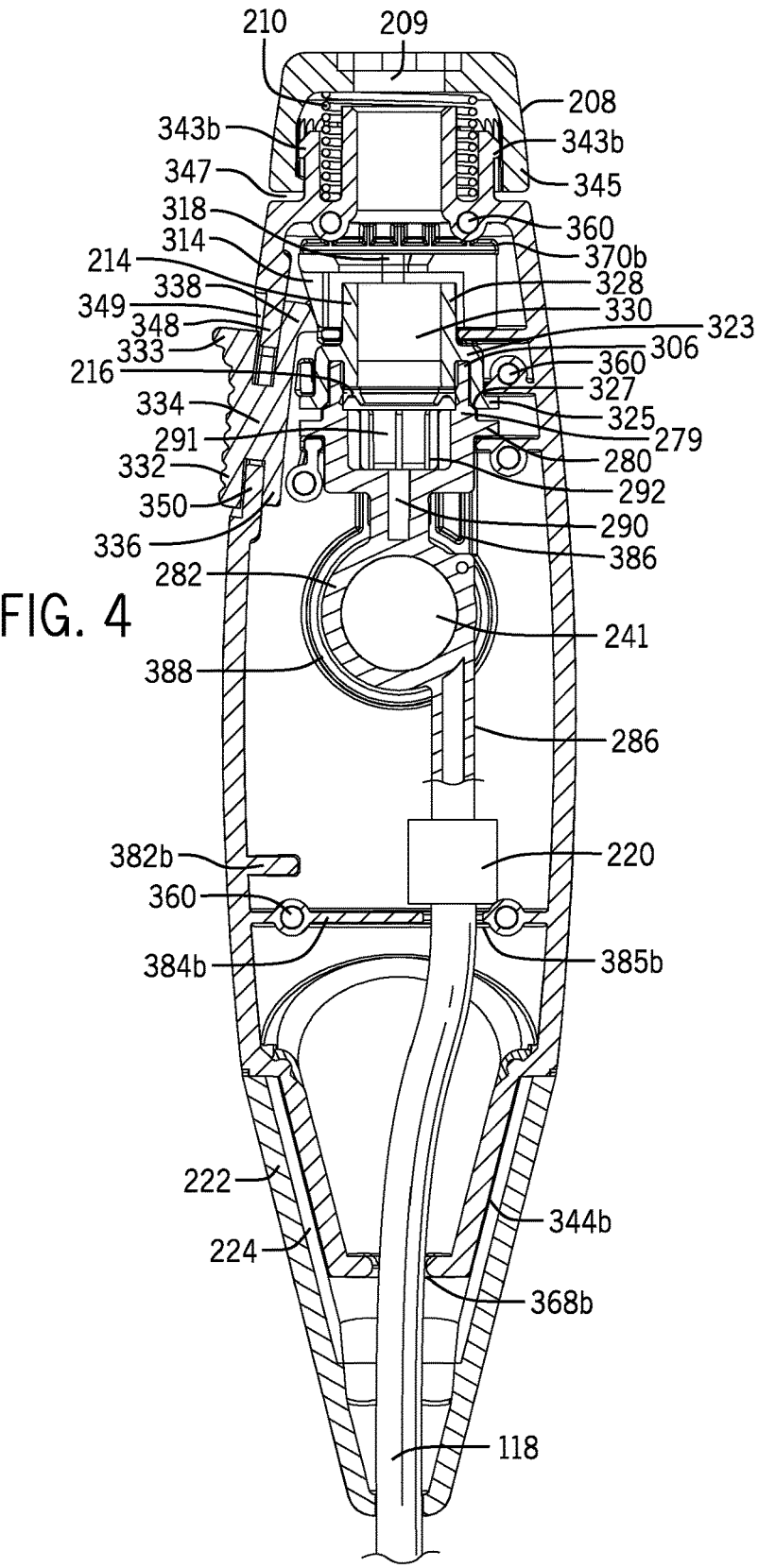
FIG. 4 is an elevation view in cross section of the handle of FIG. 2A along line 4-4 in FIG. 2D, in irrigate mode.
Figure 8D:
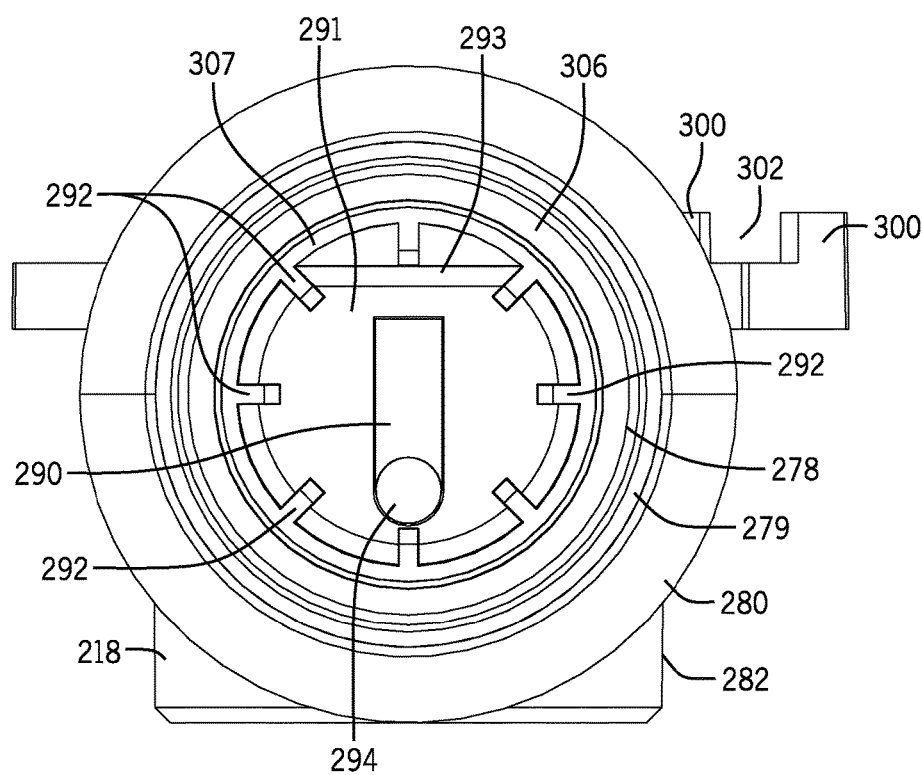
FIG. 8D is a top plan view of the valve body of FIG. 8A.

As shown in FIGS. 4 and 8D, the mouth 278 may define a cylindrical cavity. The tip receiving portion 281 positioned below the mouth 278 may be substantially cylindrical or, as depicted in FIG. 8B, may be squared off on one side by a front wall 293 to form a D-shaped cavity 291 in the tip receiving portion 281. The tip receiving portion 281 may also include interior ribs 292 extending radially inward from the curved walls of the tip receiving portion 281 and for a length in a direction generally aligned with the longitudinal axis of the handle 200. An interior wall from which the ribs 292 extend that defines the cavity 291 in the tip receiving portion 281 may be smaller in diameter than the mouth 278 and thereby form an annular ledge 307 between the mouth 278 and the tip receiving portion 281 coterminous with the height of the ribs 292. A cup seal 216 may be positioned inside the mouth 278, above the tip receiving portion 281, and proximate to the first rim 279. An outer edge of the cup seal 216 may be supported by the annular ledge 307.

A substantially keyhole-shaped well 290 may be formed in the neck 277 of the valve body 218. The well 290 may extend through the neck 277 between the fluid outlet 294 in the valve chamber 282 and the cavity 291 defined in the tip receiving portion 281 in the upper portion 274 of the valve body 218.

With reference to FIGS. 4-7, when the handle 200 is assembled, the tip receiving portion 281 is received in semicircular notches 381a, 381b of the sixth interior shelf 380a, 380b. The valve chamber 282 of the valve body 218 is positioned within or adjacent to the circular wall 388 and/or counterforts 389 of the second handle housing segment 206. The second rim 280 is positioned above and adjacent to the sixth interior shelf 380a, 380b.

Figure 9:
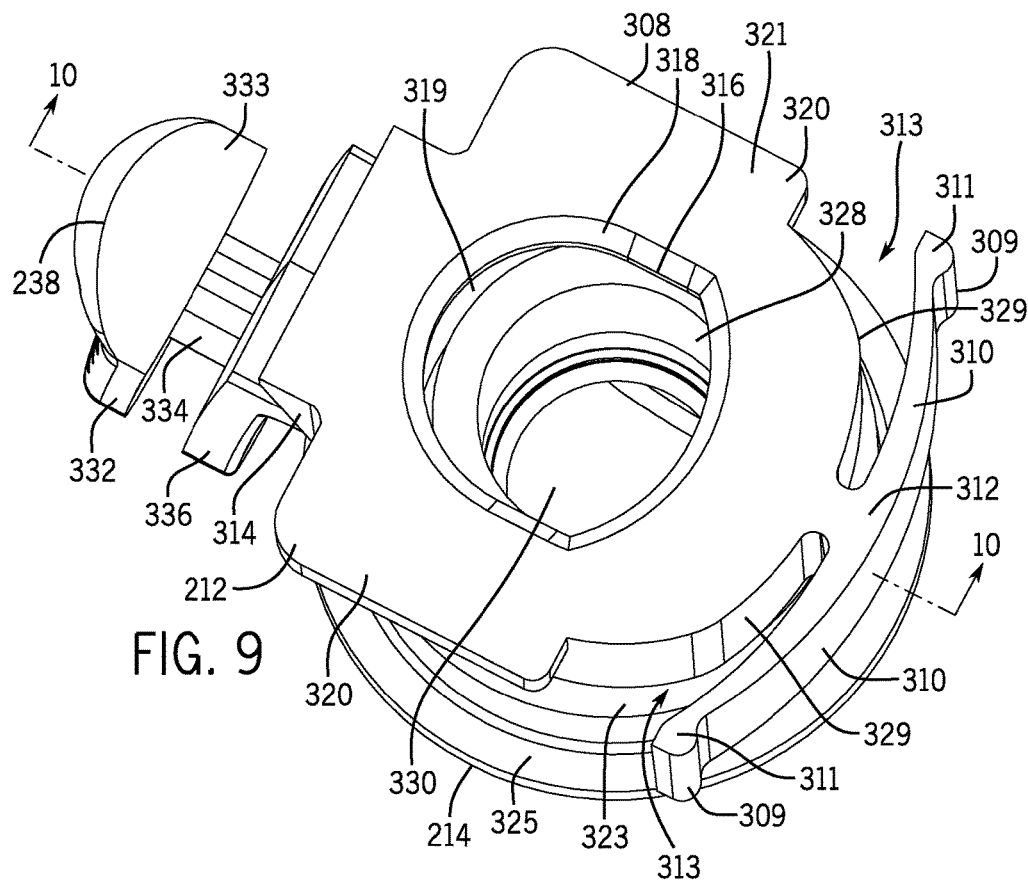
FIG. 9 is a top front right isometric view of a tip eject mechanism of the handle of FIG. 2A.
Figure 10:
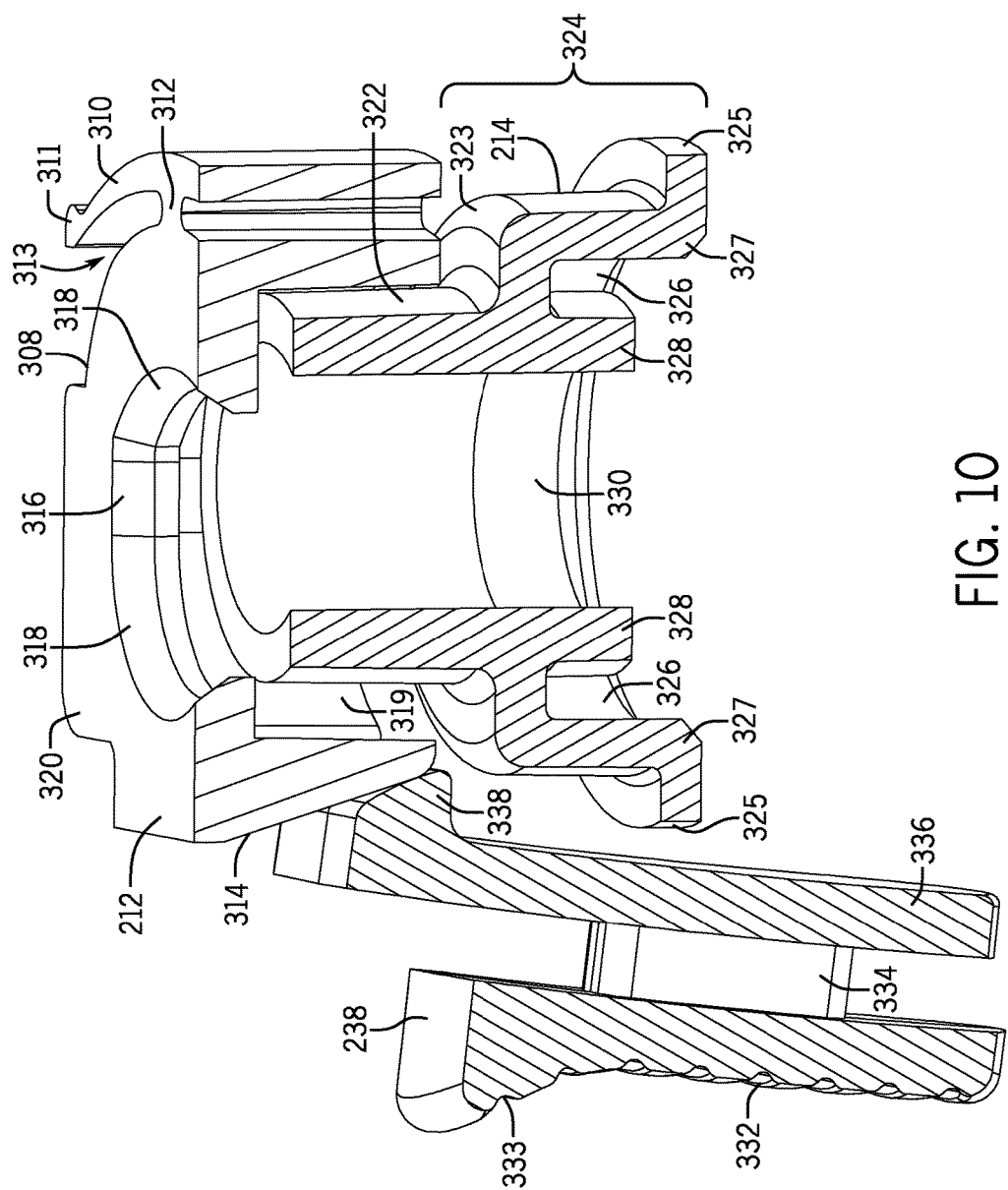
FIG. 10 is an isometric view in cross section of the tip eject mechanism of FIG. 9 along line 10-10 in FIG. 9.
Figure 13A:
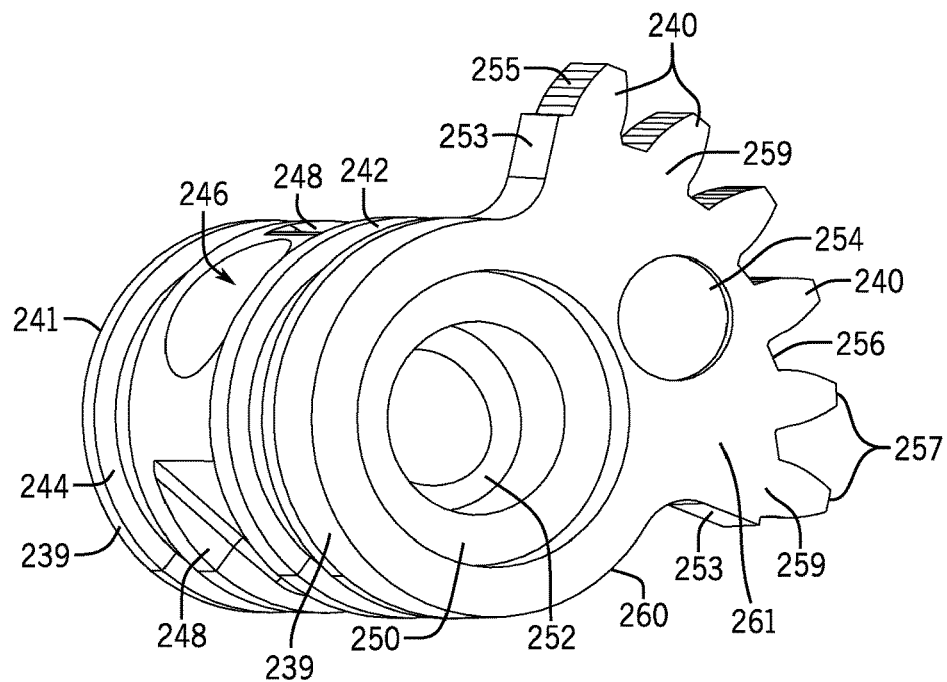
FIG. 13A is a front left isometric view of a valve gear of the handle of FIG. 2A.
Figure 13B:
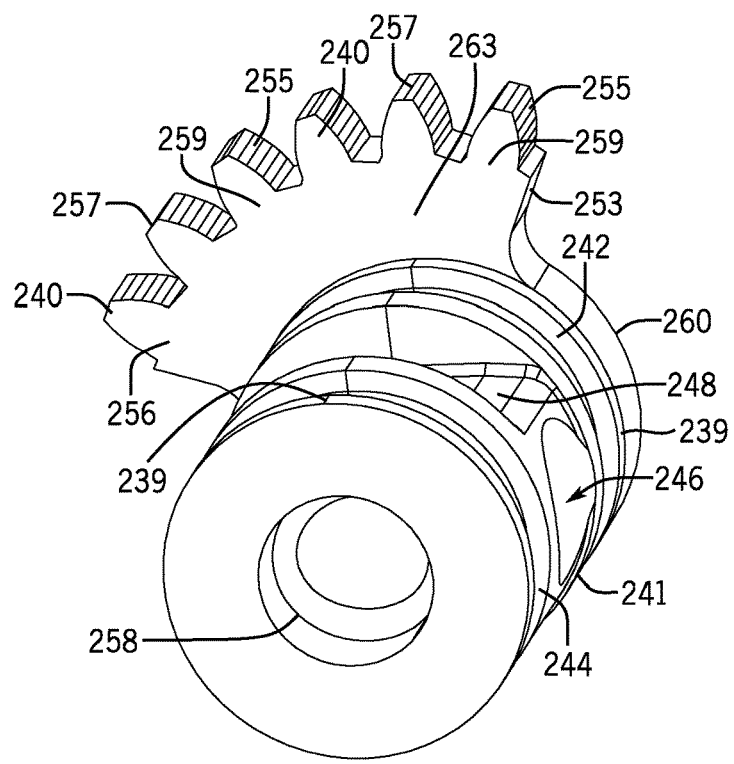
FIG. 13B is a rear left isometric view of the valve gear of FIG. 13A.
Figure 13C:
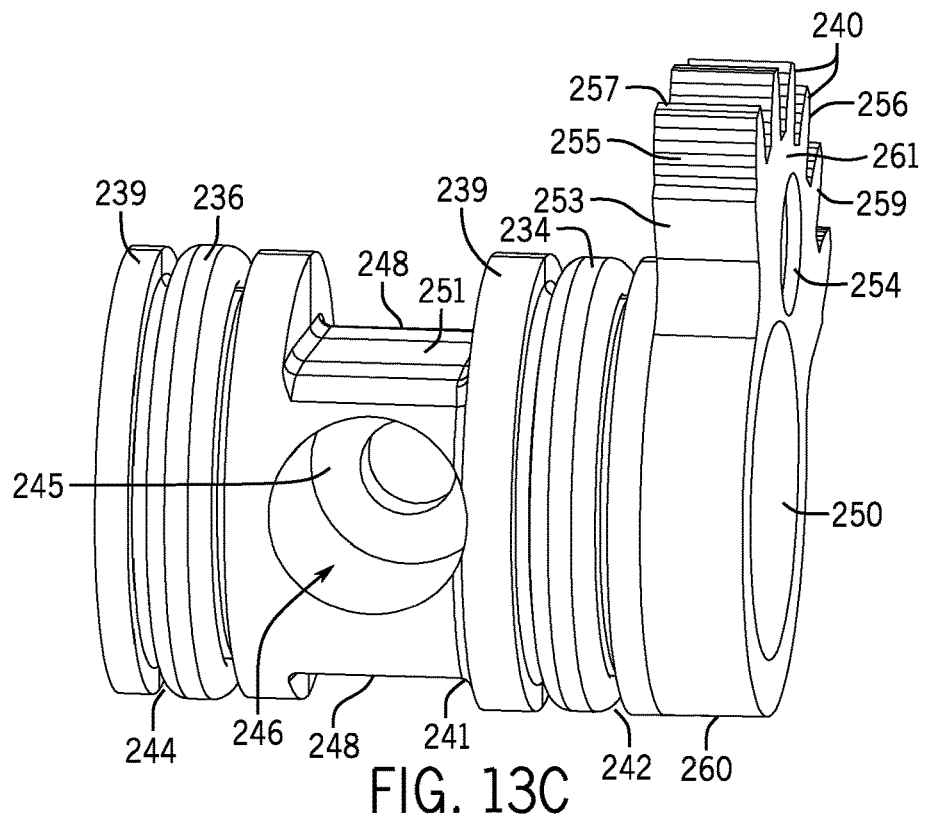
FIG. 13C is a top left isometric view of the valve gear of FIG. 13A.
Figure 13D:
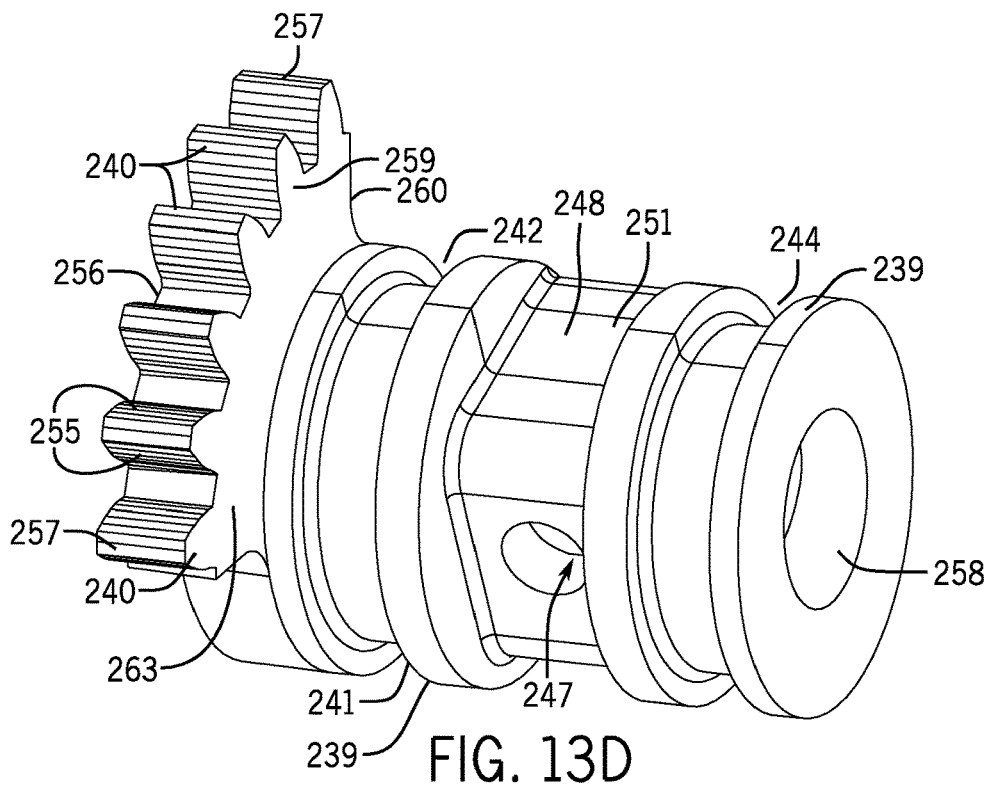
FIG. 13D is a top right isometric view of the valve gear of FIG. 13A.

As shown in FIGS. 3-5A, a valve cap 214 may be positioned on top of the mouth 278 of the valve body 218. With reference to FIGS. 9 and 10, the valve cap 214 comprises a body 322 and a skirt 324. The body 322 is generally cylindrical in shape and comprises a cavity wall 328 that defines a first tip cavity 330 for receiving a tip 114. The skirt 324 may include an annular recess 326, a hip 323, a foot 325, and a heel 327. The hip 323 may have a circumference greater than the circumference of the body 322, and the foot 325 may have a still greater circumference than that of the hip 323, which may create a stepped outer surface of the valve cap 214. The annular recess 326 is configured to receive the wall 306 of the mouth 278 of the valve body 218. The first rim 279 of the valve body 218 is positioned under the heel 327 of the foot 325 of the valve cap 214.

In the embodiment depicted in FIG. 10, the cavity wall 328 terminates above the plane created by the foot 325 of the valve cap 214. In other embodiments, the cavity wall 328 may extend to or beyond the plane created by the foot 325 of the valve cap 214. When the handle 200 is assembled, the portion of the cavity wall 328 proximal to the foot 325 may be adjacent to the cup seal 216.

With reference to FIGS. 4-7, when the handle 200 is assembled, the body 322 of the valve cap 214 is received in semicircular notches 377a, 377b in the fourth interior shelves 376a, 376b, and the skirt 324 is received in semicircular notches 379a, 379b in the fifth interior shelves 378a, 378b. The hip 323 is positioned below, and may be retained by, the fourth interior shelves 376a, 376b. Similarly, the foot 325 is positioned below, and may be retained by, the fifth interior shelves 378a, 378b. The heel 327 of the foot 325 is positioned adjacent to the first rim 279 of the upper portion 274 of the valve body 218.

Figure 11:
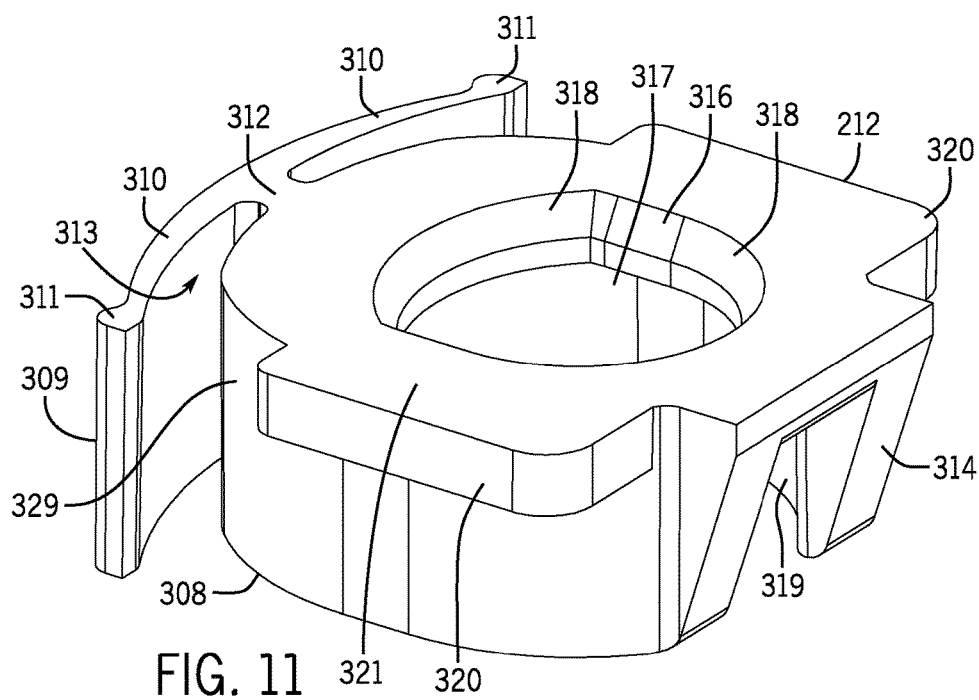
FIG. 11 is a top left isometric view of a latch of the tip eject mechanism of FIG. 9.

FIGS. 9 and 10 depict one embodiment of a tip eject mechanism of the handle 200. The tip eject mechanism or tip release assembly comprises the valve cap 214, as described above, a latch 212, and a tip eject button 238. The latch 212 may comprise a latch body 308 to which spring legs 310 are attached via a neck 312. The spring legs 310 extend laterally apart from each other on opposing sides of the neck 312 along a side of the latch body 308 opposite the tip eject button 238. The neck 312 separates the spring legs 310 from the latch body 308 such that a gap 313 is formed between each of the spring legs 310 and the latch body 308. In the exemplary embodiment shown, the outer wall 329 of the latch body 308 opposite each of the spring legs 310 is curved such that the gaps 313 widen toward their open ends away from the neck 312. Each spring leg 310 may terminate in a foot 311. The outer surface of each foot 311 may have a bulbous projection 309 outward along the width, as depicted in FIG. 11. Each spring leg 310 may be flexible, deformable, and/or resilient such that it returns to its original shape and configuration after being compressed.

Figure 5A:
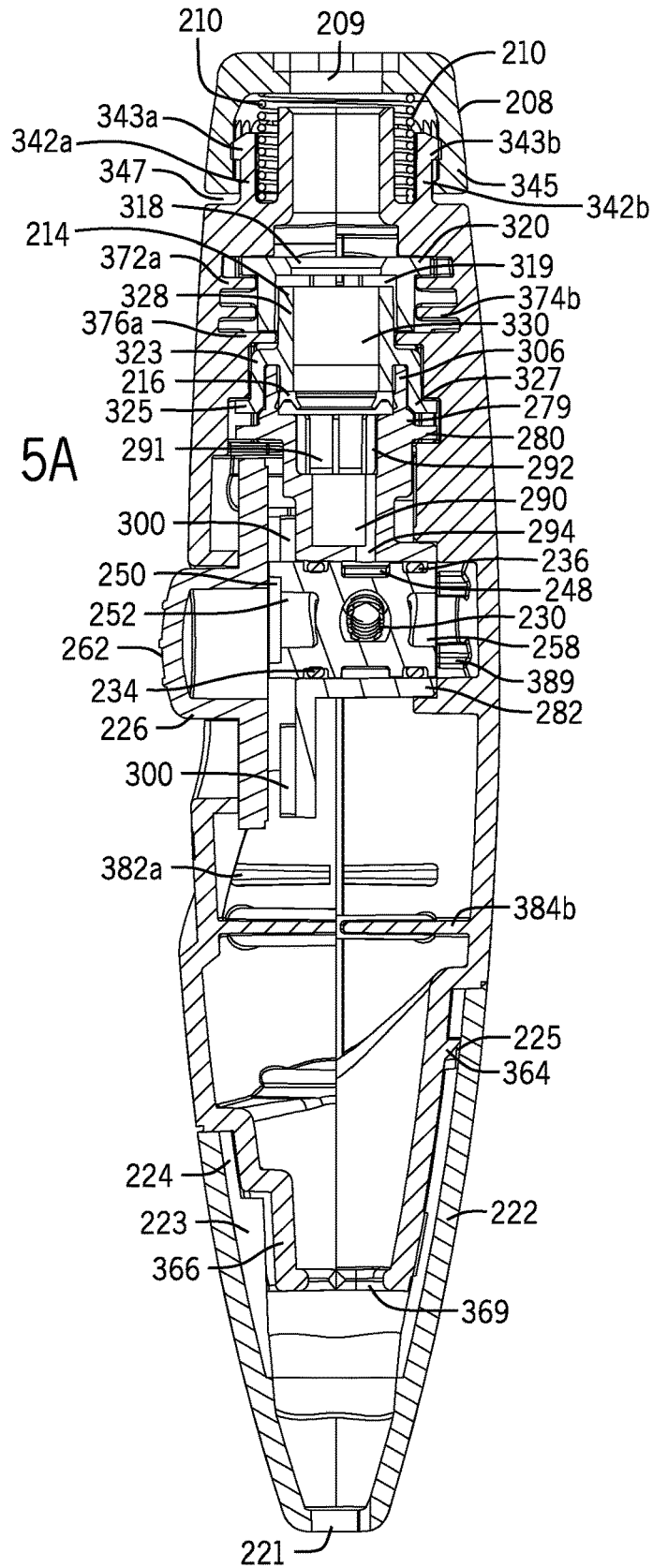
FIG. 5A is an elevation view in cross section of the handle of FIG. 2A along line 5-5 in FIG. 2A, excluding the hose and in irrigate mode.

As depicted in FIGS. 9-11, a top surface 321 of the latch body 308 comprises ledges 320 that extend laterally partially around the perimeter of the latch body 308 on the sides between the spring legs 310 and the tip eject button 238. The ledges 320 extend laterally away from the latch body 308 to a uniform or variable width. The width may be great enough at a given point along a ledge 320 that, when the handle 200 is assembled, the ledges 320 rest on the second interior shelves 372a, 372b as shown in FIG. 5A.

The latch body 308 also comprises an interior lip 318 that extends generally radially inward above an interior wall 319. The interior lip 318 may be chamfered, as depicted in FIG. 11, or may be smooth and may define a second tip-receiving aperture 316 for receiving the tip 114. The perimeter defined by the interior lip 318 may be an irregular oval or bell shape, as depicted in FIG. 11, or may be any other shape. The shape of the perimeter may be complementary to the tip 114 that is received in the second tip-receiving aperture 316.

The interior walls 319 may define a valve cap cavity 317, which is configured to receive the body 322 of the valve cap 214 (see FIG. 10). A cross-sectional area of the valve cap cavity 317 may thus be greater than a cross-sectional area of the second tip-receiving aperture 316. The valve cap cavity 317 may be substantially oval in shape and thus oblong as compared to the circular shape of the body 322 of the valve cap 214.

The latch body 308 also includes a chamfered wall 314 on the sidewall opposite the neck 312 and spring legs 310. The chamfered wall 314 may include an opening between two chamfered legs, as depicted in FIG. 11, or it may be solid.

With reference to FIGS. 4-7, when the handle 200 is assembled, the top of the latch 212 may be below and adjacent to the first interior shelves 370a, 370b, and at least a portion of the bottom of the latch 212 may be adjacent to or rest upon the fourth interior shelves 376a, 376b. As described above, the ledges 320 of the latch body 308 may rest on the second interior shelves 372a, 372b.

In the embodiment depicted in FIG. 10, the tip eject button 238 comprises the exterior slider portion 332 connected to the interior slider portion 336 via a neck 334. The exterior slider portion 332 may be substantially oval in shape. The exterior slider portion 332 may also have a ribbed or grooved outer surface, and may include a raised stop 333, some of all of which help provide traction for a user's finger or hand to more easily operate the tip eject button 238 and prevent the user's finger or hand from slipping off the tip eject button 238.

The interior slider portion 336 may be longer than exterior slider portion 332, as in the embodiment depicted in FIG. 10, or may be shorter than or approximately the same length as the exterior slider portion 332. The interior slider portion 336 includes a nose 338 that interfaces with, and has an angle complimentary to, the chamfered wall 314 of the latch 212.

In the embodiment depicted in FIGS. 2D, 4, 6, and 7, and as described above, when the handle 200 is assembled, the exterior slider portion 332 of the tip eject button 238 is configured to be received in the pocket 349 of the first and second handle housing segments 204, 206; the neck 334 is configured to be received in the opening 352; and the interior slider portion 336 is secured by the upper and lower surfaces 348, 350 of the pocket 349.

With reference now to FIGS. 3 and 12A-12C, the handle 200 may also comprise a pause control actuator 226, which may include a button 262, a first flange 266, and a second flange 268. Although depicted in FIG. 12A as round with ribs 264 and raised from the face of the pause control actuator 226, the button 262 may be any size or shape, and have any texture that helps provide traction against a user's finger or hand. The face of each of the first and second flanges 266, 268 on the same side of the pause control actuator 226 as the button 262 may be substantially rectangular and flat.

With reference to FIGS. 12B and 12C, one of the flanges, such as the first flange 266, may have a substantially rectangular cuboid shape. The face of the opposing flange, i.e., the second flange 268, on the opposite side of the pause control actuator 226 as the button 262 includes a rack gear 270. The rack gear 270 comprises one or more rack gear teeth 272 that extend laterally in the direction of the first flange 266. The rack gear teeth 272 may be aligned with one another as they extend along the longitudinal or straight edge of the actuator. Part or all of the edge 267 of each rack gear tooth 272 may be chamfered. The width of the base 271 of a rack gear tooth 272 may be wider than the tip 273 of that rack gear tooth 272. The width of one or both of the base 271 and tip 273 may be less than the width of that rack gear tooth 272 between the base 271 and the tip 273. The plane of a tip 273 may be flat and parallel to the plane of its base 271, as shown in FIGS. 12B and 12C, or the tip 273 may be rounded or pointed. Nine rack gear teeth 272 are depicted in the embodiment of FIGS. 12B and 12C, but any number of rack gear teeth 272 may be present. The rack gear teeth 272 may be substantially evenly spaced along the length of the rack gear 270.

In some embodiments, and as depicted in FIGS. 3, 13A-D, and 14, the handle 200 includes a valve gear assembly that comprises the pause control actuator 226, as described above, the valve spool 228, a ball spring 230, and a ball 232.

The valve spool 228, which may be a spool housing a ball valve, comprises at least a spool body 241 and a gear portion 260. The spool body 241 may have lateral cylindrical portions 239 that define annular recesses 242, 244, each for receiving an O-ring 234, 236 or other seal. The O-rings 234, 236 may help prevent fluid, including pressurized fluid, from leaking into the handle housing 202 along the interface of the spool body 241 and the valve chamber 282 of the valve body 218 when the spool body 241 is positioned inside the valve body 218, as described below.

Figure 5B:
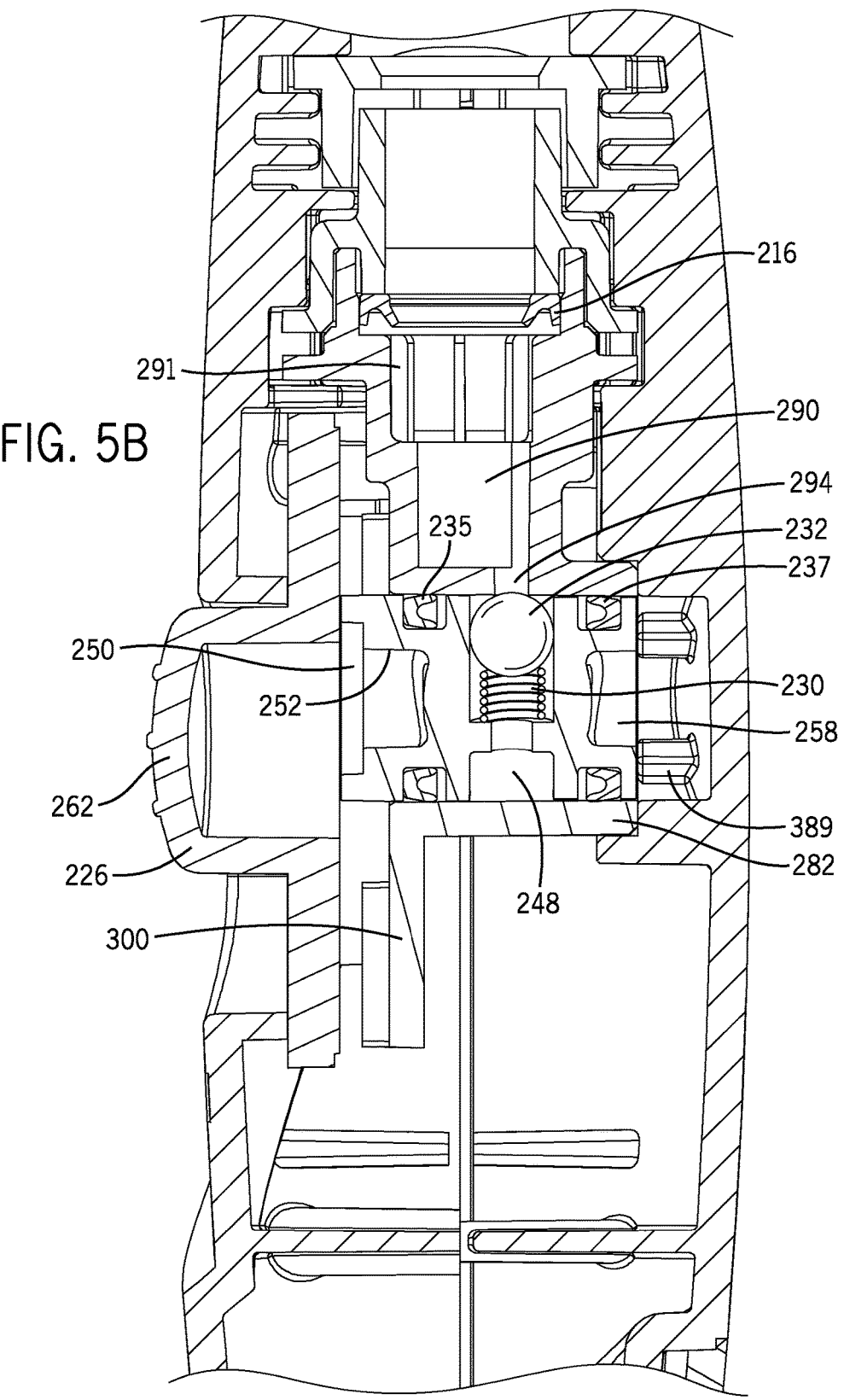
FIG. 5B is an enlarged cross section view similar to FIG. 5A illustrating another example of a sealing element for the valve spool and with the valve spool in the closed position.

With reference to FIG. 5B, in other embodiments, the valve spool 228 may include other types of sealing components positioned with the annular recesses 242, 244. In one example, a first U-cup 235 and a second U-cup 237 may be positioned in the annular recesses 242, 244, respectively. In this embodiment, the U-cups 235, 237 may reduce the force required by a user to move the actuator as compared to embodiments including the O-rings 234, 236. Additionally, the compressibility of the U-cups 235, 237 as compared to the O-rings 234, 236 provides for a "smoother" actuation feel when a user activates the valve, as described in more detail below.

With reference again to FIGS. 13A and 13B, a cylindrical cavity 246 may be formed in a sidewall of the spool body 241 between the cylindrical portions 239. An outer perimeter surface of the spool body 241 defining the cavity 246 is of the same diameter and follows the curvature of the cylindrical portions 239. An interior wall 245 may define a base of the cavity 246. The interior wall 245 may further define a central aperture 247 therethrough such that the interior wall 245 takes the form of an annular shelf in the base of the cavity 246. The central aperture 247 is smaller in diameter than the diameter of the cavity 246. The cavity 246 is configured to receive a ball spring 230 and a ball 232, which may be a rubber or elastomeric ball 232.

When the valve gear assembly is assembled, the ball spring 230 may be positioned adjacent to the interior wall 245. The ball 232 has a diameter at least marginally less than the diameter of the cavity 246 but greater than the diameter of the central aperture 247, and is positioned within the cavity 246 against the ball spring 230.

The spool body 241 may also define a channel 248 conducting fluid. The channel 248 may be formed between the cylindrical portions 239. In the exemplary embodiment depicted in FIGS. 13A-13D, the channel 248 traverses approximately three quarters of the circumference of the spool body 241. The channel 248 does not traverse the cavity 246, but does traverse, and therefore intersect with, the central aperture 247. The channel 248 may have a flat base 251, or the base 251 may be curved along a shorter radius from the center axis of the spool body 241 than the radius of the cylindrical portions 239.

The spool body 241 may also include one or more recesses or cavities 250, 252, 254, 258, which may be substantially circular in shape and may have varying depths. In the exemplary embodiment, these recesses may be artifacts of the molding process, for example, to reduce wall thicknesses and provide uniform cooling of the molded material forming the spool body 241, but otherwise may not have any particular role with respect to the function of the valve spool 228.

The gear portion 260 of the valve spool 228 is positioned adjacent one of the cylindrical portions 239 and may be generally circular in shape with a radially extending, arcuate pinion gear 256. The pinion gear 256 may have an outer face 261 and an inner face 263. The pinion gear 256 comprises one or more pinion gear teeth 240 that extend generally radially away from the spool body 241 at one end. The arc of the pinion gear 256 may be bounded laterally by sidewalls 253. Part or all of the edges 255 of each pinion gear tooth 240 may be chamfered. The width of a base 259 of a pinion gear tooth 240 may be wider than a tip 257 of that pinion gear tooth 240. Each tip 257 may be flat and generally parallel to a plane of its base 259, as shown in FIGS. 13A-13D, or the tip 257 may be rounded or pointed. Six pinion gear teeth 240 are depicted in the embodiment of FIGS. 13A-13D, but any number of pinion gear teeth 240 may be provided. The pinion gear teeth 240 may be substantially evenly spaced along the arc-length of the pinion gear 256.

Figure 14:
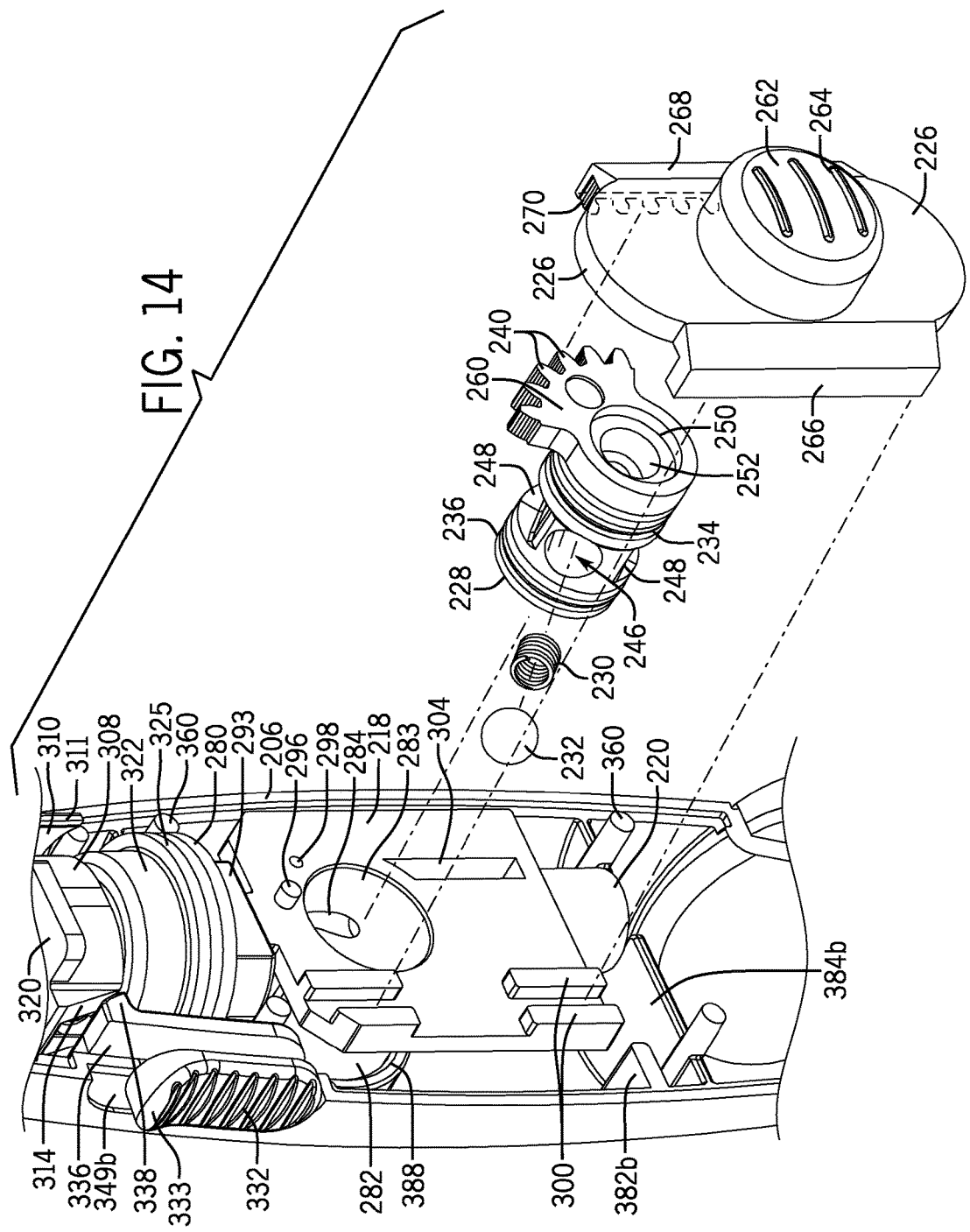
FIG. 14 is an exploded isometric view of the valve gear assembly of the handle of FIG. 2A.

With reference to FIGS. 5A and 14, when the handle 200 is assembled, the ball spring 230 and ball 232 are inserted into the cavity 246 of the spool body 241 and O-rings 234, 236 are positioned in the annular recesses 242, 244 of the spool body 241. The spool body 241 may be inserted through the valve chamber aperture 283 and positioned within the valve chamber 282 of the lower portion 276 of the valve body 218. The O-rings 234, 236 create a fluid-tight seal between the valve spool 228 and the valve chamber 282.

With reference to FIG. 5B, in embodiments including U-cups 235, 237 rather than the O-rings 234, 236, the U-cups 235, 237 may be received into the annular recesses 242, 244 of the spool body 241. Similar to the O-rings 234, 236, the U-cups 235, 237 act to seal against the valve spool 228 and the valve chamber 282. However, unlike the O-rings 234, 236, the U-cups 235, 237 may not require as significant of a force to overcome the compression of the sealing material against the valve chamber 282 to allow the pause switch to be activated by a user. In particular, if the valve spool 228 sits for a long period of time without being activated, the O-rings 234, 236 become somewhat difficult to compress when the switch is activated. In examples including the U-cups 235, 237 the force required by the user is reduced, even when the switch has not been activated for an extended prior of time. This is because the U-cups may be easier to compress and more flexible than the O-rings. These features also allow the U-cups 235, 237 provide a "smoother" feedback feel to the user as compared to the O-rings as they may slide easier against the valve chamber 282 wall due to their external shape, which provides an enhanced user experience.

The ball 232 may be positioned adjacent to the chamber wall 285, and the ball 232 may compress the ball spring 230 against the interior wall 245 of the spool body 241 of the valve spool 228. The ball 232 is thus biased toward the chamber wall 285 to create a fluid-tight seal over the fluid outlet 294 in the valve body 218 when the ball 232 is positioned adjacent thereto.

The gear portion 260 of the valve spool 228 extends out of the valve chamber aperture 283 in the valve body 218. The inner face 263 of the pinion gear 256 may be flush with the surface of the valve 218 body defining the valve chamber aperture 283 and the teeth 240 of the pinion gear 256 may be oriented opposite and extend away from the walls 300 on the lower portion 276 of the valve body 218.

The first flange 266 of the pause control actuator 226 may be received in the slot 302 created by the walls 300 of the lower portion 276 of the valve body 218. The rack gear 270 of the pause control actuator 226 is operably associated with the pinion gear 256 of the gear portion 260 of the valve spool 228 via mating or interfacing of some or all of the rack gear teeth 272 with some or all of the pinion gear teeth 240.

When the handle 200 is assembled, and the pause control actuator 226 is moved upwards toward the collar 208, rotation of the pinion gear 256 is stopped when the button 262 of pause control actuator 226 contacts the first handle housing segment 204, and/or when the upper sidewall 253 of the pinion gear 256 contacts the post 296. When the pause control actuator 226 is moved downwards, sliding of the rack gear 270 is stopped when the button 262 contacts the first handle housing segment 204, and/or when the first flange 266 contacts the seventh interior shelf 382a, 382b.

Insertion and Ejection of a Tip

A user may insert a tip 114 into, and eject a tip 114 from, the handle 200 of the oral irrigator 100 of FIGS. 1-18 according to the following procedures.

Figure 15:
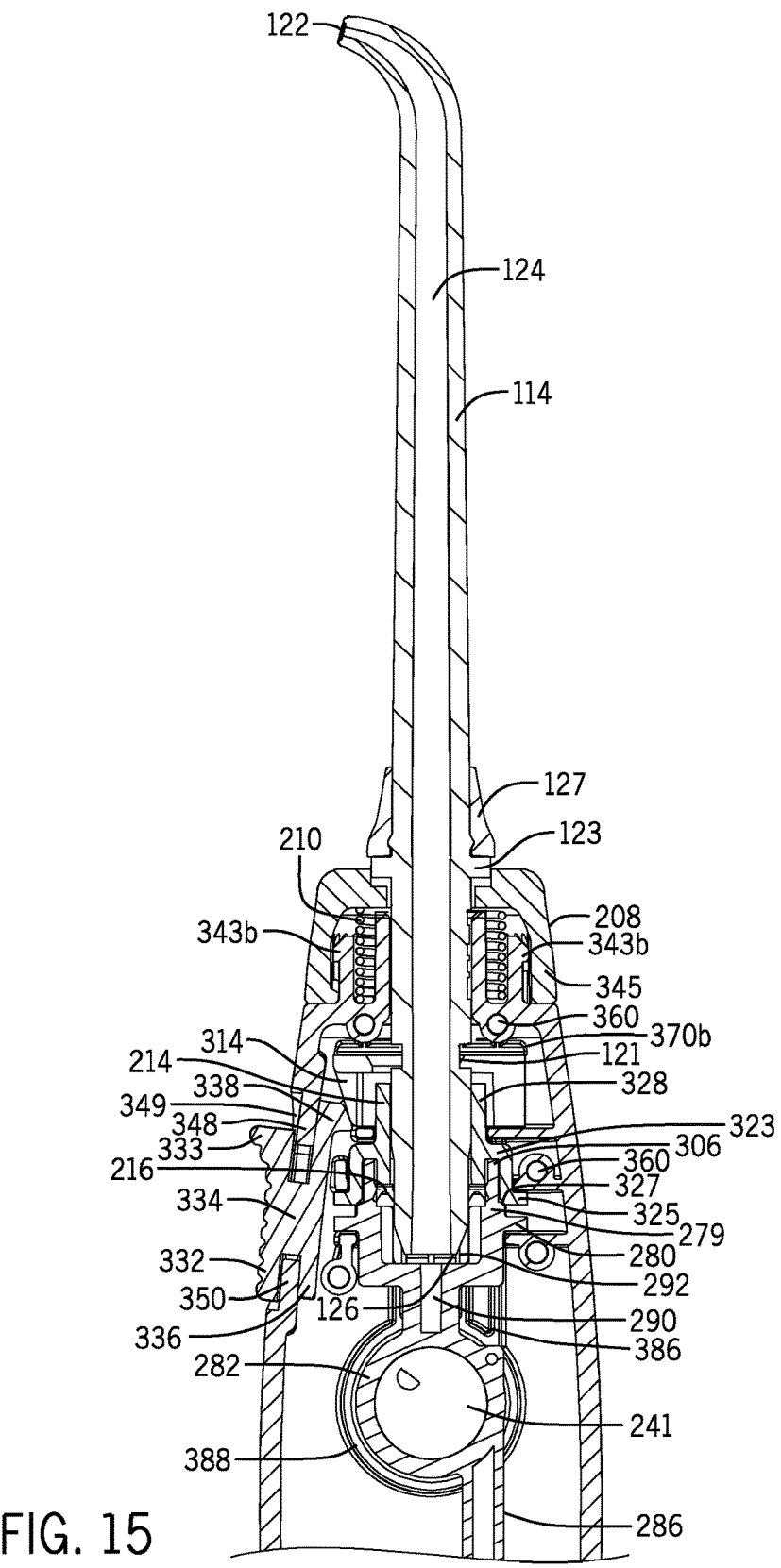
FIG. 15 is an elevation view in cross section of the handle of FIG. 2A along line 15-15 in FIG. 2C, in irrigate mode, with a tip inserted.
Figure 16:
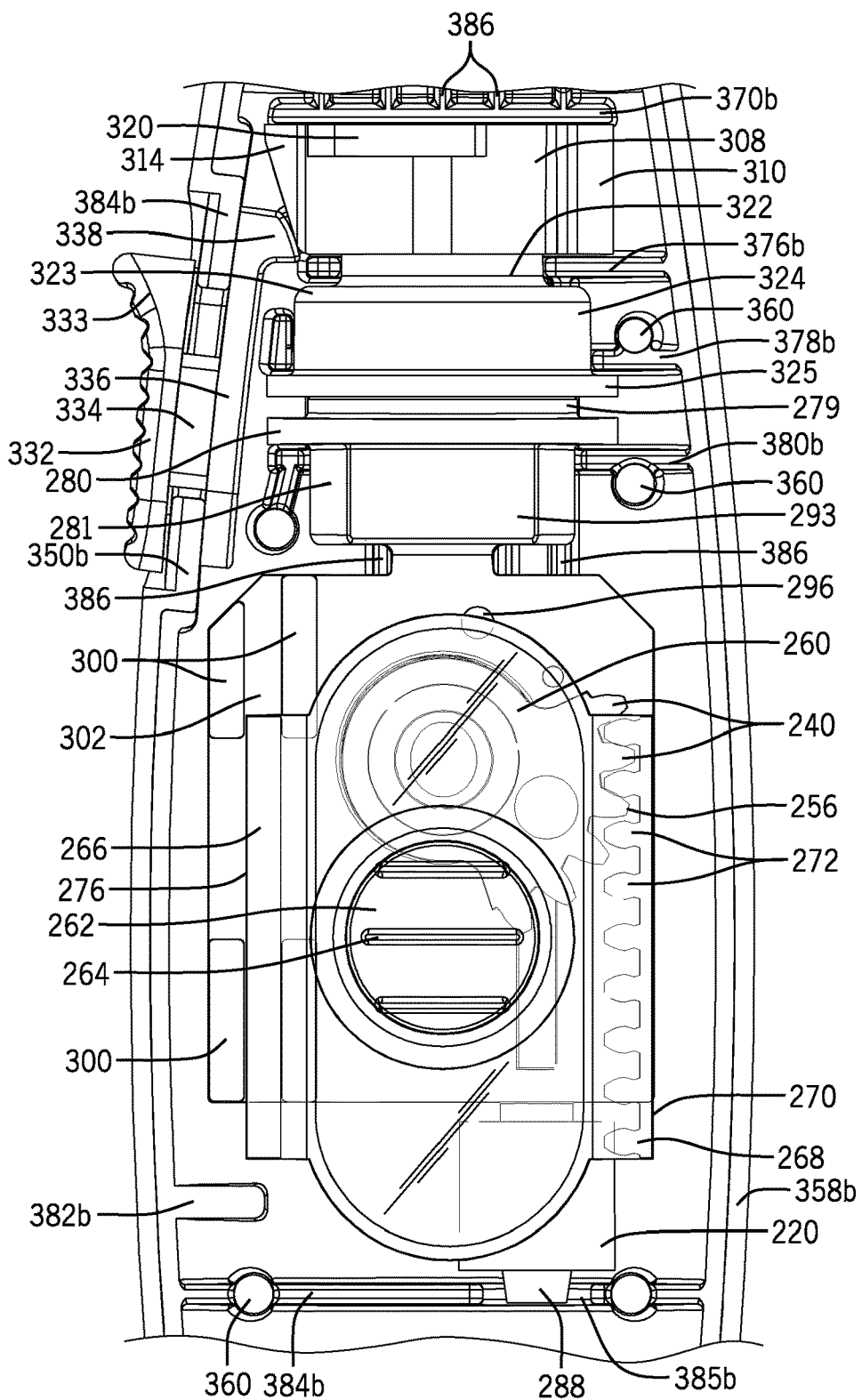
FIG. 16 is a front elevation view of a portion of the handle of FIG. 2A, in pause mode, with the front housing removed.
Figure 17A:
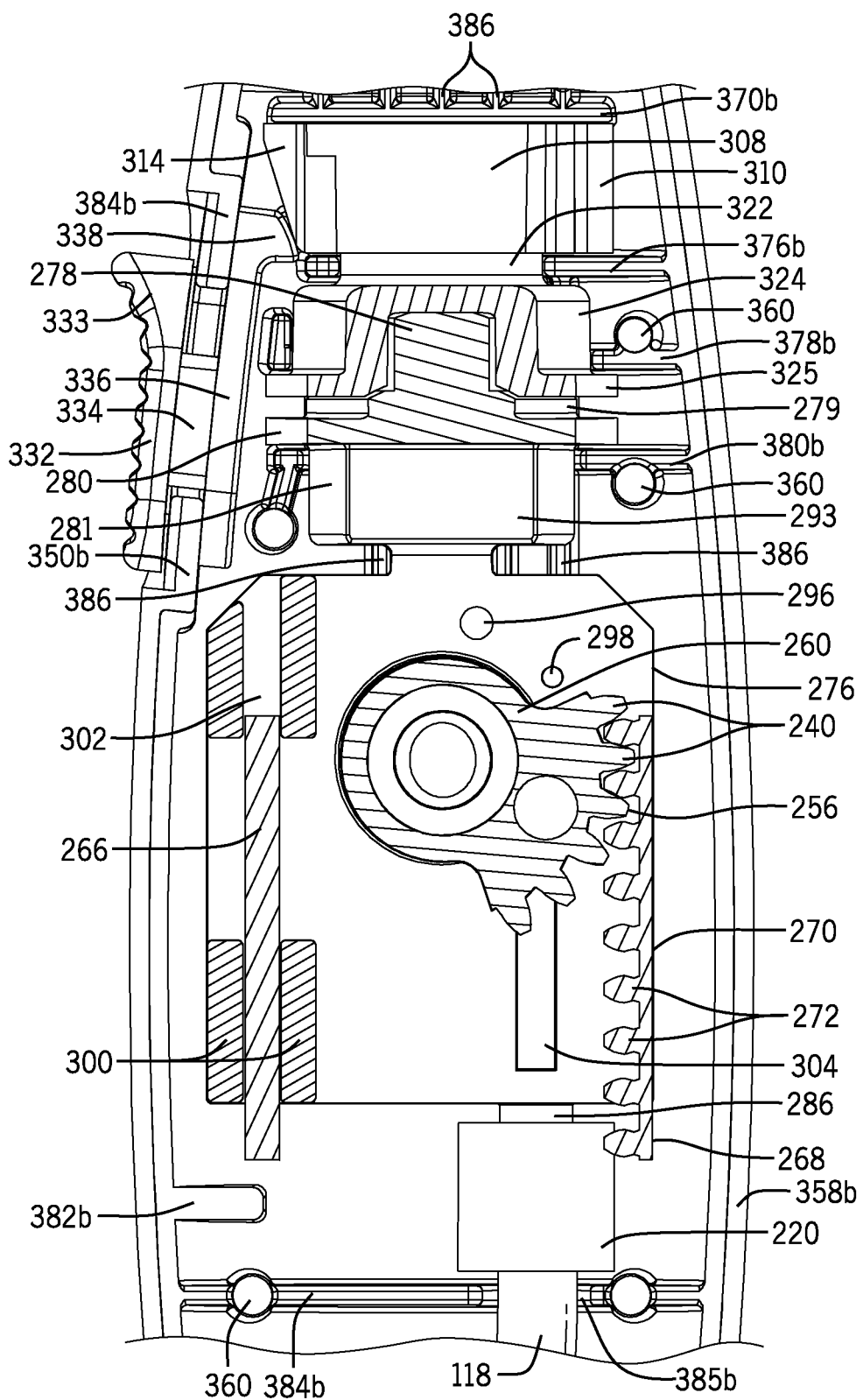
FIG. 17A is a front elevation view in cross section of a portion of the handle of FIG. 2A along line 17A-17A in FIG. 2C, in pause mode.
Figure 17B:
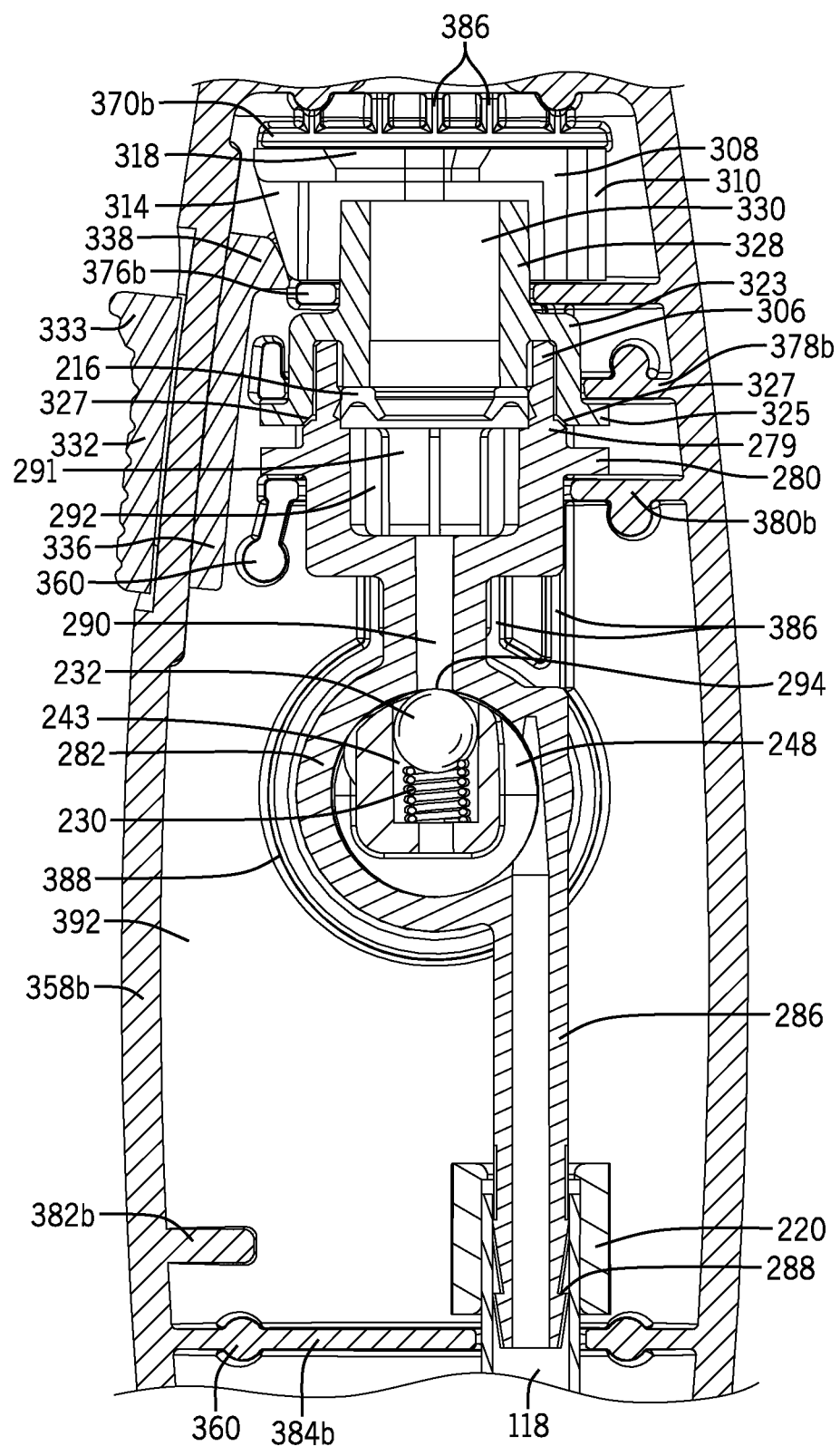
FIG. 17B is front elevation view in cross section of a portion of the handle of FIG. 2A along line 17B-17B in FIG. 2C, in pause mode.
Figure 18A:
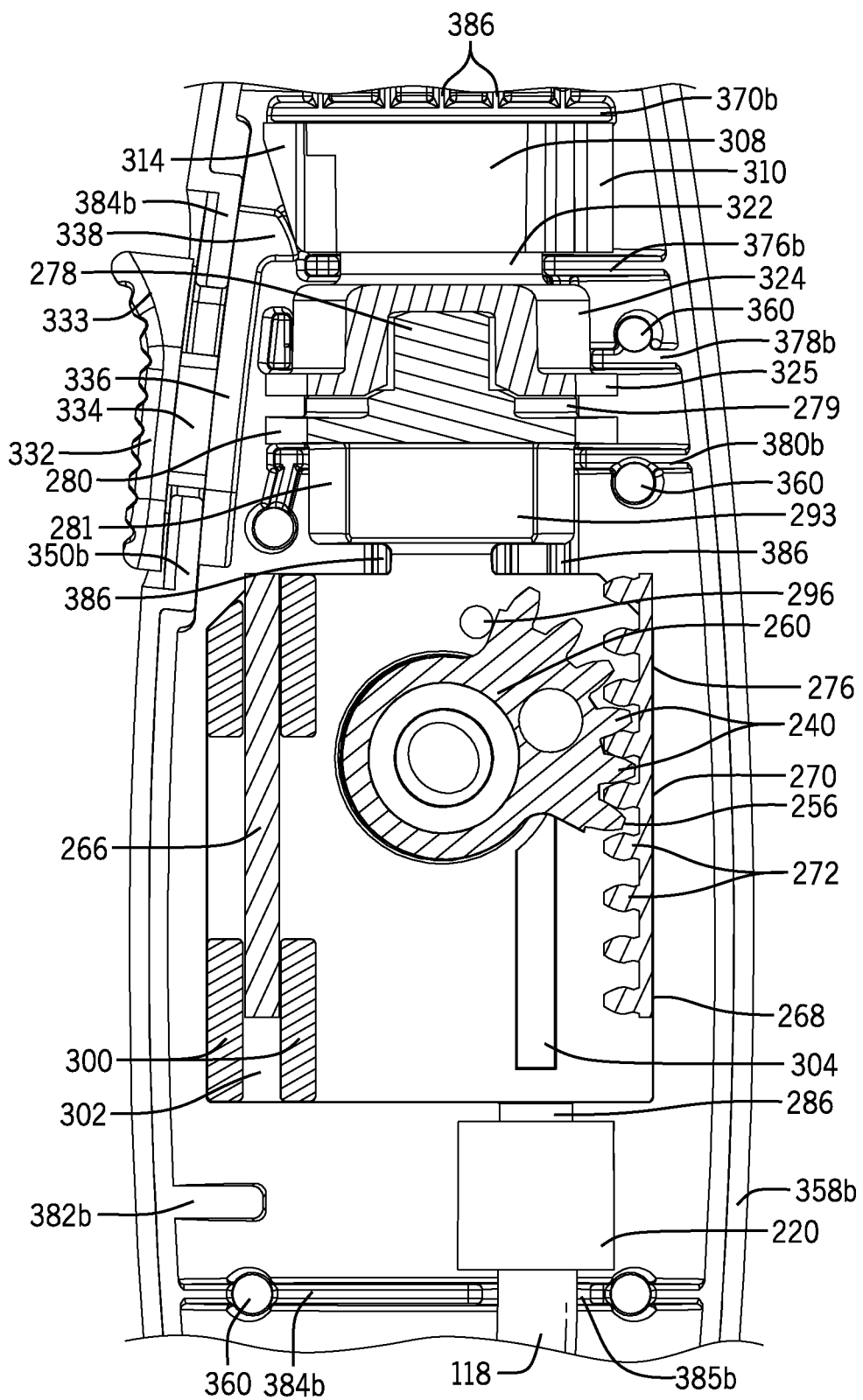
FIG. 18A is a front elevation view in cross section of a portion of the handle of FIG. 2A along line 18A-18A in FIG. 2D, in irrigate mode.
Figure 18B:
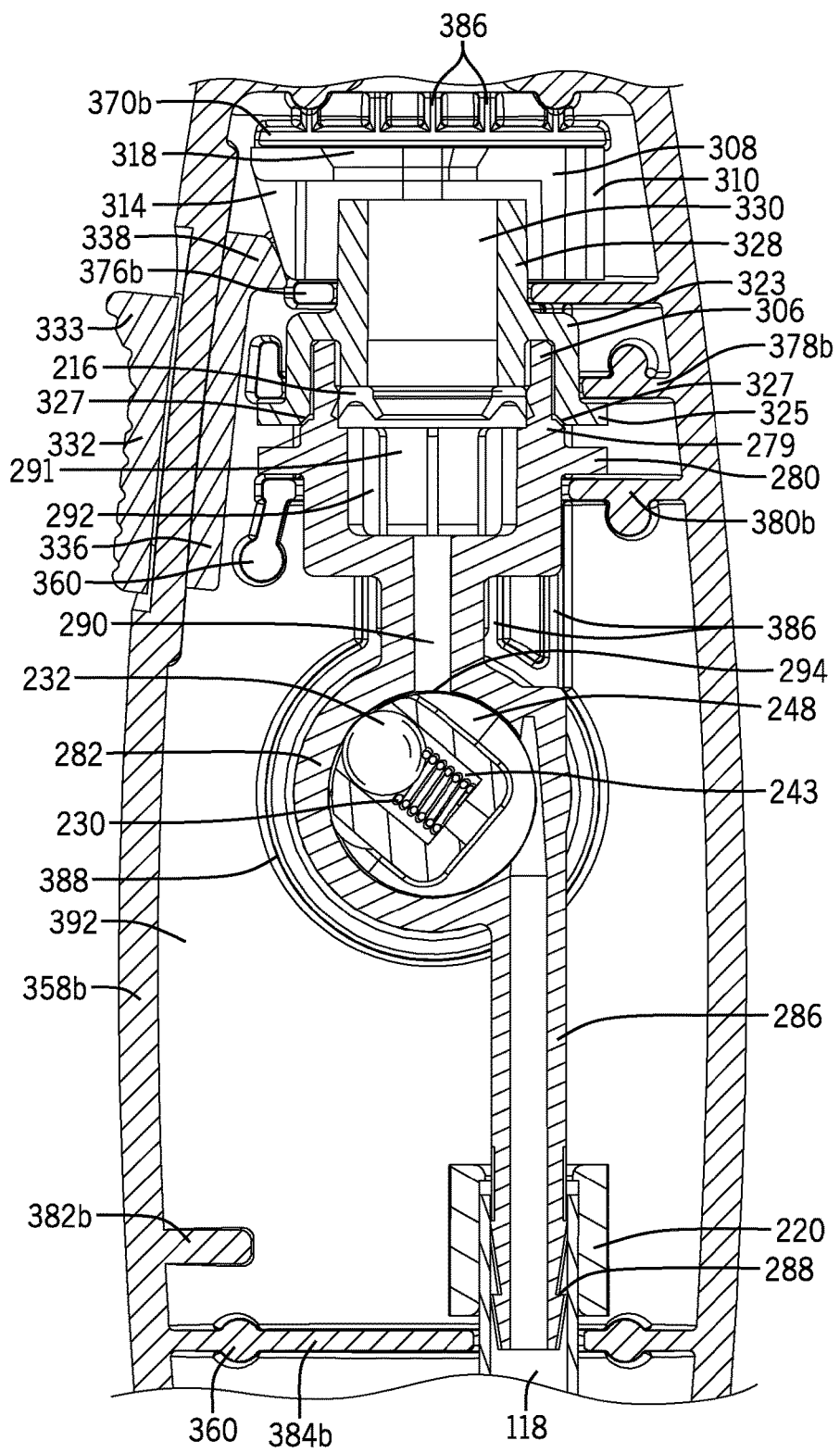
FIG. 18B is a front elevation view in cross section of a portion of the handle of FIG. 2A along line 18B-18B in FIG. 2D, in irrigate mode.

A tip 114 is inserted into the handle 200 by passing a proximal end 126 of the tip 114 through the first tip-receiving aperture 209 of the collar 208, through the tip receiving portions 341a, 341b of the first and second handle housing segments 204, 206, and into the second tip-receiving aperture 316 of the latch body 308 (see FIG. 15). Before the tip 114 enters the handle 200, the second tip-receiving aperture 316 of the latch body 308 is partially offset from the first tip cavity 330 of the valve cap 214, which is positioned below the second tip-receiving aperture 316. The tip 114 engages the latch body 308 and pushes the interior lip 318 of the latch body 308 laterally in the direction of the spring legs 310 until the second tip-receiving aperture 316 of the latch body 308 and the first tip cavity 330 of the valve cap 214 vertically align. The spring legs 310 are compressed, and the feet 311 are positioned adjacent to the recessed portions 373a, 373b, 375a, 375b of the second and third interior shelves 372a, 372b, 374a, 374b.

The proximal end 126 of the tip 114 can then proceed through the first tip cavity 330 of the valve cap 214, past the cup seal 216, and into the cavity 291 of the tip receiving portion 281 of the upper portion 274 of the valve body 218. A tip collar 127 on the tip 114 may be biased against the collar 208 when the tip 114 has been fully inserted into the handle 200. The well 290 may help fluid to flow into a tip 114 even when the fluid outlet 294 is not positioned directly below the fluid inlet of the tip 114. For example, as shown in FIG. 8D, the fluid outlet 294 is positioned off-center in the neck 277, but the well 290 transfers the fluid flow into the center of the cavity 291 in the tip receiving portion 281 and thus under the fluid inlet of the tip 114. The outer diameter of the proximal end 126 of the tip 114 is slightly larger than the inner diameter of the cup seal 216, thereby creating a fluid-tight seal between the cup seal 216 and the tip 114. The D-shape of the perimeter of the interior lip 318 of the latch body 308, and the shape of the interior surface of the tip receiving portion 281, either or both of which are complimentary or keyed to the D-shape of the proximal end 126 of the tip 114, help to align the tip 114 in the handle 200. The tip 114 may also be aligned with and/or supported by the interior ribs 292 of the tip receiving portion 281. The tip 114 may be coupled to the latch 212 by capturing the interior lip 318 of the latch body 308 within an annular recess 121 of the tip 114.

The collar 208 of the handle 200 is depressed toward the bodies 340a, 340b of the first and second handle housing segments 204, 206 when the tip 114 is coupled with the latch 212. As the collar 208 is depressed, the arcuate tabs 345 of the collar 208 move along the necks 342a, 342b of the first and second handle housing segments 204, 206 toward the bodies 340a, 340b, which decreases the height of the gap 347, and the first spring 210 is compressed. The compressed first spring 210 exerts an upward force, which will return the collar 208 back to its original position (i.e., separated from the bodies 340a, 340b by a gap 347) in the absence of another force opposing this upward force. When the tip 114 is coupled with the latch 212, this upward force will be opposed by a flange 123 on the tip 114 that holds the collar 208 down, thereby maintaining the collar 208 in a position adjacent the handle housing 202.

An audible click or other similar noise may occur when the latch 212 captures the annular recess 121 of the tip 114, thereby providing an audible indication that the tip 114 is attached to the handle 200. The noise may be mechanically produced (for example, a click resulting from a portion of the tip 114 impacting a portion of the handle 200, or a click resulting from a portion of the tip 114 springing outward or mechanically deforming).

In another example of inserting a tip 114, a user slides the exterior slider portion 332 of the tip eject button 238 upwards toward the collar 208 of the handle 200, and maintains the exterior slider portion 332 in that position while inserting a tip 114 into the handle 200 as described above. Sliding the exterior slider portion 332 upwards along the longitudinal axis of the handle housing also slides the interior slider portion 336 upwards via the connection between the exterior and interior slider portions 332, 336 at the neck 334. As the nose 338 of the interior slider portion 336 slides upwards along the chamfered wall 314 of the latch body 308, the nose 338 forces the latch 212 to move laterally in the direction of the spring legs 310. The second tip-receiving aperture 316 of the latch body 308 is thus aligned over the first tip cavity 330 of the valve cap 214 before the tip 114 is inserted. The inserted tip 114 can then proceed into the cavity 291 as described above.

A user ejects a tip 114 by sliding the exterior slider portion 332 of the tip eject button 238 upward toward the collar 208. As the nose 338 of the interior slider portion 336 slides upwards along the chamfered wall 314 of the latch body 308, the nose 338 forces the latch 212 to move laterally in the direction of the spring legs 310. In other words, the latch 212 moves substantially normal or perpendicular to the movement of the tip eject button. The interior lip 318 disengages from the annular recess 121 in the tip 114 and the tip 114 is decoupled. The spring force of the first spring 210 on the collar 208 helps to eject the tip 114 by forcing the collar 208 upward against the flange 123 of the tip 114.

As noted, when the tip 114 is decoupled, the force opposing the upward force exerted by the first spring 210 is removed, thereby allowing the first spring 210 to move the collar 208 back to its original position. This movement of the collar 208 from a position adjacent to the bodies 340a, 340b to its original position provides a visual indication that the tip 114 has been decoupled from the latch 212.

Operation of the Oral Irrigator

A user may use the oral irrigator 100 and components of FIGS. 1-18 for oral irrigation and/or cleaning of the teeth, gums, and tongue according to the following procedure.

Once a tip 114 is connected to the handle 200 as described above, and the reservoir 104 is filled and connected to the base 102, the oral irrigator 100 can be used. To activate the oral irrigator 100, the use selects the first control actuator 112, which provides power to the motor to activate the pump. The pump pulls fluid from the reservoir 104 and forces it through the hose connector 125 into the hose 118.

Fluid flows through the hose 118 into the first fluid inlet 289 in the terminus of the barbed tip 288, and through the fluid conduit 286 of the valve body 218 towards the second fluid inlet 284 in the valve chamber 282 of the lower portion 276 of the valve body 218.

When the valve spool 228 is in the open position (see FIGS. 18A and 18B), fluid flows from the second fluid inlet 284 into and around the channel 248 of the spool body 241. From the channel 248, fluid flows into the fluid outlet 294 in the valve chamber 282, and into the well 290 that extends between the fluid outlet 294 and the tip receiving portion 281 in the upper portion 274 of the valve body 218. Fluid can then enter the proximal end 126 of the tip 114, which is positioned in the cavity 291 of the tip receiving portion 281, and exit the tip outlet 122 into the user's mouth.

During use, the user may select one or more of the second, third, and pause control actuators 110, 113, 226 on the oral irrigator 100 or handle 200 to vary one or more characteristics of the fluid flow output from the tip 114. For example, the second control actuator 110 may be selected to vary fluid pressure of the fluid as it exits the tip 114 or the third control actuator 113 may be selected to activate a massage mode.

Irrigate Mode and Pause Mode

During irrigate mode, fluid flows to the tip 114 as described above when the valve gear assembly is placed in an open position as follows (see FIGS. 4, 5A, 18A and 18B). When the pause control actuator 226 including the rack gear 270 is positioned toward the collar 208 (i.e., in the up or on position), the pinion gear 256 of the gear portion 260 of the valve spool 228, which is operably connected to the rack gear 270, is moved to a position proximate to the post 296 and covers the aperture 298. In this position of the valve spool 228, the cavity 246 of the spool body 241 is positioned such that the ball 232 is not pressed against the fluid outlet 294 and therefore does not block the path of fluid through the valve body 218. The channel 248 of the spool body 241 is positioned such that it fluidly connects the second fluid inlet 284 in the valve chamber 282 of the lower portion 276 of the valve body 218 to the fluid outlet 294 in the valve chamber 282.

During pause mode, no fluid flows into or out of the tip 114. To initiate pause mode without turning off power to the oral irrigator 100, the valve gear assembly must be moved to a closed position as follows (see FIGS. 5B, 16, 17A, and 17B). A user manually slides the pause control actuator 226 downward relative to the housing by sliding the button 262 away from the collar 208 (i.e., in the down or off position), which also slides the rack gear 270 downward. In other words, the user slides the actuator substantially along a longitudinal axis of the housing. This translational movement of the rack gear 270 is converted to rotational movement of the operably associated pinion gear 256 via the interlocked rack gear teeth 272 and pinion gear teeth 240. The pinion gear 256 is thus rotated clockwise away from the post 296, which rotates the operably connected spool body 241, including the cavity 246. In other words, the longitudinal or lateral movement of the actuator along the handle housing is translated or converted into rotational movement of the spool. By this rotation, the ball 232 in the cavity 246 is thus brought into a position below the fluid outlet 294. The ball 232 partially or completely covers the fluid outlet 294, which partially or completely blocks fluid from flowing into the fluid outlet 294 and thereby pauses or stops fluid flow through the valve body 218 to the tip 114.

While fluid flow is paused, the force of the compressed ball spring 230 against the ball 232 helps to maintain the ball 232 securely positioned against the fluid outlet 294 and helps the ball 232 create a fluid-tight seal. Fluid may enter the cavity 246 beneath the ball 232 through the central aperture 247 in the interior wall 245. Fluid pressure against the ball 232 may also help to maintain the ball 232 securely positioned against the fluid outlet 294.

The pause mode is selected by mechanical, not electrical, operation of the pause control actuator 226. A mechanically selectable pause mode avoids the need for electrical circuitry in the handle 200, which thereby helps improve the safety of the handle 200 and the oral irrigator 100 because electrical circuits are not in close physical proximity to fluid conduits. A mechanically instead of an electrically controlled pause mode also decreases the manufacturing cost of the handle 200 and the oral irrigator 100. No separate battery is required in the handle 200 to power such circuits. Alternatively, the handle 200 need not be electrically wired to the base unit of the oral irrigator 100. Thus, an easily accessible and selectable pause mode is provided to the user with significantly less manufacturing cost and greater safety.

All directional references (e.g., upper, lower, upward, downward, left, right, leftward, rightward, top, bottom, above, below, vertical, horizontal, clockwise, and counter-clockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

What is claimed is:

1. An oral irrigator handle comprising
   a housing;
   a fluid inlet into the housing;
   a fluid outlet from the housing;
   a valve body positioned between the fluid inlet and the fluid outlet, the valve body defining a valve inlet in fluid communication with the fluid inlet of the housing and a valve outlet in fluid communication with the valve inlet and in selective fluid communication with the fluid outlet of the housing;
   a valve spool positioned within the valve body;
   a sealing assembly connected to the spool and movable therewith; and
   a mechanical pause control actuator that interfaces with the valve spool, wherein actuation of the mechanical pause control actuator moves the valve spool from an open position to a paused position within the valve body, wherein in the paused position, the sealing assembly seals the valve outlet to interrupt fluid flow from the valve inlet to the fluid outlet of the housing.

2. The oral irrigator handle of claim 1, wherein the valve spool comprises a pinion gear extending from an outer surface of the valve spool.

3. The oral irrigator handle of claim 2, wherein the mechanical pause control actuator comprises a rack gear, wherein the pinion gear forms an engagement with the rack gear, such that when the mechanical pause control actuator is actuated the engagement between the rack gear and the pinion gear converts a first type of motion to a second type of motion.

4. The oral irrigator handle of claim 3, wherein the mechanical pause control actuator is actuated by moving linearly relative to the valve body.

5. The oral irrigator of claim 4, wherein the first type of motion is linear motion and the second type of motion is rotational motion.

6. The oral irrigator handle of claim 5, wherein rotation of the pinion gear rotates the valve spool to move the valve spool to the paused position.

7. The oral irrigator handle of claim 1, wherein the sealing assembly further comprises
   a biasing element connected to the valve spool; and
   a ball seated on a top end of the biasing element such that the biasing element biases the ball towards the valve body, wherein in the paused position of the valve spool, the ball blocks a passageway between the fluid inlet and the fluid outlet.

8. The oral irrigator handle of claim 1, wherein the valve spool further comprises:
   an annular recess; and
   a sealing component adjacent the annular recess to provide a seal between the handle along an interface of the valve spool.

9. An oral irrigator comprising
   a reservoir;
   a pump in fluid communication with the reservoir;
   a handle in fluid communication with the pump, comprising a housing, a handle inlet into the housing and a handle outlet from the housing; and
   a pause switch assembly connected to the handle comprising
      an actuator slidably connected to the handle and movable between a first position and a second position; and
      a valve assembly connected to the actuator and positioned between the handle inlet and the handle outlet, the valve assembly comprising:
         a valve body received within a cavity of the handle, the valve body defining a valve chamber having a valve inlet in fluid communication with the handle inlet and a valve outlet in fluid communication with the valve inlet and the handle outlet; and
         a spool rotatably connected to the actuator and received within the valve chamber; and
         a sealing assembly connected to the spool and rotatable therewith; wherein
      movement of the actuator from the first position to the second position rotates the spool of the valve assembly from an open position to a paused position; and
      in the paused position, the sealing assembly seals the valve outlet to prevent fluid flow between the valve inlet and the handle outlet.

10. The oral irrigator of claim 9, wherein the pause switch assembly is independent from the pump.

11. The oral irrigator of claim 9, wherein
    the actuator comprises a plurality of actuator gear teeth extending from a first interior side;
    the spool comprises a plurality of spool gear teeth extending from a first surface thereof, wherein the spool gear teeth mesh with the actuator gear teeth to translate a linear motion of the actuator to a rotational motion of the spool within the valve chamber.

12. The oral irrigator of claim 11, wherein the spool gear teeth extend in an arc pattern along the first surface of the spool.

13. The oral irrigator of claim 12, wherein the first interior side is a linear edge.

14. The oral irrigator of claim 9, wherein the valve assembly further comprises at least one U-cup received around the spool, wherein the at least one U-cup defines a seal between walls of the valve chamber and the spool.

15. The oral irrigator of claim 9, wherein the sealing assembly comprises
a spring connected to the spool; and
a ball seated on a top end of the spool, wherein the spring biases the ball against a wall of the valve chamber.

16. The oral irrigator of claim 15, wherein the ball and the spring are received within a cavity defined on an outer surface of the spool.

17. A handle for an irrigating device comprising
a housing in fluid communication with a fluid source and comprising a housing inlet and a housing outlet;
a tip removably connected to the housing and in fluid communication with the housing outlet; and
a pause switch connected to the housing and configured to selectively interrupt fluid flow from the housing outlet to the housing inlet, the pause switch comprising
a switch movable along a longitudinal axis of the housing between a first position and a second position;
a valve body received within the housing, the valve body defining a valve inlet in fluid communication with the housing inlet and a valve outlet in fluid communication with the valve inlet and the housing outlet;
a valve member rotatably coupled to the switch and received within the valve body; and
a sealing assembly connected to the valve member and rotatable therewith; wherein
movement of the switch from the first position to the second position rotates the valve member and the sealing assembly from an open position to a paused position; and
in the open position the fluid flows uninterrupted from the housing inlet to the tip; and
in the paused position the sealing assembly seals the valve outlet such that the fluid flow is blocked between the housing inlet and the tip.

18. The handle of claim 17, wherein the sealing assembly comprises a ball and a spring.

* * * * *